(12) United States Patent
Jager et al.

(10) Patent No.: US 7,622,568 B2
(45) Date of Patent: Nov. 24, 2009

(54) ISOLATED NUCLEIC ACID MOLECULES ENCODING CANCER ASSOCIATED ANTIGENS, THE ANTIGENS PER SE, AND USES THEREOF

(75) Inventors: Dirk Jager, Frankfurt am Main (DE); Elisabeth Stockert, NY, NY (US); Matthew Scanlan, NY, NY (US); Alexander Knuth, Frankfurt am Main (DE); Lloyd Old, NY, NY (US); Ali Gure, NY, NY (US); Yao-Tseng Chen, NY, NY (US); Elke Jager, Frankfurt am Main (DE)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 11/985,028

(22) Filed: Nov. 12, 2007

(65) Prior Publication Data
US 2008/0177031 A1    Jul. 24, 2008

Related U.S. Application Data

(60) Division of application No. 10/181,663, filed on Feb. 24, 2003, now abandoned, which is a continuation-in-part of application No. 09/602,362, filed on Jun. 22, 2000, now Pat. No. 6,911,529, which is a continuation-in-part of application No. 09/451,739, filed on Nov. 30, 1999, now Pat. No. 6,774,226.

(51) Int. Cl.
    *C07H 21/02*    (2006.01)
(52) U.S. Cl. .................................. 536/23.1; 536/23.5
(58) Field of Classification Search ..................... None
    See application file for complete search history.

(56) References Cited

U.S. PATENT DOCUMENTS

2002/0018766 A1 *    2/2002    Roberts et al. ............ 424/93.21

OTHER PUBLICATIONS

Smith DR. submission to GenEMBL, Apr. 27, 2000, Acession No: AC067744, Version AC067744.6.*

* cited by examiner

*Primary Examiner*—Misook Yu
*Assistant Examiner*—Mark Halvorson
(74) *Attorney, Agent, or Firm*—Fulbright & Jaworski LLP

(57) ABSTRACT

The invention relates to newly identified cancer associated antigens. It has been discovered that each of these molecules provokes antibodies when expressed by a subject. The ramifications of this observation are also a part of this invention.

10 Claims, No Drawings

ISOLATED NUCLEIC ACID MOLECULES ENCODING CANCER ASSOCIATED ANTIGENS, THE ANTIGENS PER SE, AND USES THEREOF

RELATED APPLICATIONS

This application is a divisional application of Ser. No. 10/181,663, filed Feb. 24, 2003, now abandoned which is a continuation in part of Ser. No. 09/602,362, filed Jun. 22, 2000 now U.S. Pat. No. 6,911,529 which is a continuation in part of Ser. No. 09/451,739, filed Nov. 30, 1999, now U.S. Pat. No. 6,774,226 both of which are incorporated by reference in their entirety.

FIELD OF THE INVENTION

This invention relates to antigens associated with cancer, the nucleic acid molecules encoding them, as well as the uses of these.

BACKGROUND AND PRIOR ART

It is fairly well established that many pathological conditions, such as infections, cancer, autoimmune disorders, etc., are characterized by the inappropriate expression of certain molecules. These molecules thus serve as "markers" for a particular pathological or abnormal condition. Apart from their use as diagnostic "targets", i.e., materials to be identified to diagnose these abnormal conditions, the molecules serve as reagents which can be used to generate diagnostic and/or therapeutic agents. A by no means limiting example of this is the use of cancer markers to produce antibodies specific to a particular marker. Yet another non-limiting example is the use of a peptide which complexes with an MHC molecule, to generate cytolytic T cells against abnormal cells.

Preparation of Such Materials, of Course, Presupposes a Source of the Reagents Used to generate these. Purification from cells is one laborious, far from sure method of doing so. Another preferred method is the isolation of nucleic acid molecules which encode a particular marker, followed by the use of the isolated encoding molecule to express the desired molecule.

Two basic strategies have been employed for the detection of such antigens, in e.g., human tumors. These will be referred to as the genetic approach and the biochemical approach. The genetic approach is exemplified by, e.g., dePlaen et al., Proc. Natl. Sci. USA 85: 2275 (1988), incorporated by reference. In this approach, several hundred pools of plasmids of a cDNA library obtained from a tumor are transfected into recipient cells, such as COS cells, or into antigen-negative variants of tumor cell lines which are tested for the expression of the specific antigen. The biochemical approach, exemplified by, e.g., O. Mandelboim, et al., Nature 369: 69 (1994) incorporated by reference, is based on acidic elution of peptides which have bound to MHC-class I molecules of tumor cells, followed by reversed-phase high performance liquid chromography (HPLC). Antigenic peptides are identified after they bind to empty MHC-class I molecules of mutant cell lines, defective in antigen processing, and induce specific reactions with cytotoxic T-lymphocytes. These reactions include induction of CTL proliferation, TNF release, and lysis of target cells, measurable in an MTT assay, or a $^{51}$Cr release assay.

These two approaches to the molecular definition of antigens have the following disadvantages: first, they are enormously cumbersome, time-consuming and expensive; and second, they depend on the establishment of cytotoxic T cell lines (CTLs) with predefined specificity.

The problems inherent to the two known approaches for the identification and molecular definition of antigens is best demonstrated by the fact that both methods have, so far, succeeded in defining only very few new antigens in human tumors. See, e.g., van der Bruggen et al., Science 254: 1643-1647 (1991); Brichard et al., J. Exp. Med. 178: 489-495 (1993); Coulie, et al., J. Exp. Med. 180: 35-42 (1994); Kawakami, et al., Proc. Natl. Acad. Sci. USA 91: 3515-3519 (1994).

Further, the methodologies described rely on the availability of established, permanent cell lines of the cancer type under consideration. It is very difficult to establish cell lines from certain cancer types, as is shown by, e.g., Oettgen, et al., Immunol. Allerg. Clin. North. Am. 10: 607-637 (1990). It is also known that some epithelial cell type cancers are poorly susceptible to CTLs in vitro, precluding routine analysis. These problems have stimulated the art to develop additional methodologies for identifying cancer associated antigens.

One key methodology is described by Sahin, et al., Proc. Natl. Acad. Sci. USA 92: 11810-11913 (1995), incorporated by reference. Also, see U.S. Pat. No. 5,698,396, and application Ser. No. 08/479,328, filed on Jun. 7, 1995 and Jan. 3, 1996, respectively. All three of these references are incorporated by reference. To summarize, the method involves the expression of cDNA libraries in a prokaryotic host. (The libraries are secured from a tumor sample). The expressed libraries are then immunoscreened with absorbed and diluted sera, in order to detect those antigens which elicit high titer humoral responses. This methodology is known as the SEREX method ("Serological identification of antigens by Recombinant Expression Cloning"). The methodology has been employed to confirm expression of previously identified tumor associated antigens, as well as to detect new ones. See the above referenced patent applications and Sahin, et al., supra, as well as Crew, et al., EMBO J. 144: 2333-2340 (1995).

This methodology has been applied to a range of tumor types, including those described by Sahin et al., supra, and Pfreundschuh, supra, as well as to esophageal cancer (Chen et al., Proc. Natl. Acad. Sci. USA 94: 1914-1918 (1997)); lung cancer (Güre et al., Cancer Res. 58: 1034-1041 (1998)); colon cancer (Ser. No. 08/948,705 filed Oct. 10, 1997) incorporated by reference, and so forth. Among the antigens identified via SEREX are the SSX2 molecule (Sahin et al., Proc. Natl. Acad. Sci. USA 92: 11810-11813 (1995); Tureci et al., Cancer Res. 56: 4766-4772 (1996); NY-ESO-1 Chen, et al., Proc. Natl. Acad. Sci. USA 94: 1914-1918 (1997); and SCP1 (Ser. No. 08/892,705 filed Jul. 15, 1997) incorporated by reference. Analysis of SEREX identified antigens has shown overlap between SEREX defined and CTL defined antigens. MAGE-1, tyrosinase, and NY-ESO-1 have all been shown to be recognized by patient antibodies as well as CTLs, showing that humoral and cell mediated responses do act in concert.

It is clear from this summary that identification of relevant antigens via SEREX is a desirable aim. The inventors have applied this methodology and have identified several new antigens associated with cancer, as detailed in the description which follows.

DETAILED DESCRIPTION OF PREFERRED EMBODIMENTS

EXAMPLE 1

The SEREX methodology, as described by, e.g., Sahin, et al., Proc. Natl. Acad. Sci. USA 92: 11810-11813 (1995); Chen, et al., Proc. Natl. Acad. Sci. USA 94: 1914-1918 (1997), and U.S. Pat. No. 5,698,396, all of which are incorporated by reference. In brief, total RNA was extracted from a sample of a cutaneous metastasis of a breast cancer patient (referred to as "BR11" hereafter), using standard CsCl guanidine thiocyanate gradient methodologies. A cDNA library was then prepared, using commercially available kits designed for this purpose. Following the SEREX methodology referred to supra, this cDNA expression library was amplified, and screened with either autologous BR11 serum which had been diluted to 1:200, or with allogeneic, pooled serum, obtained from 7 different breast cancer patients, which had been diluted to 1:1000. To carry out the screen, serum samples were first diluted to 1:10, and then preabsorbed with lysates of *E. coli* that had been transfected with naked vector, and the serum samples were then diluted to the levels described supra. The final dilutions were incubated overnight at room temperature with nitrocellulose membranes containing phage plaques, at a density of 4-5000 plaque forming units ("pfus") per 130 mm plate.

Nitrocellulose filters were washed, and incubated with alkaline phosphatase conjugated, goat anti-human Fcγ secondary antibodies, and reactive phage plaques were visualized via incubation with 5-bromo-4-chloro-3-indolyl phosphate and nitroblue tetrazolium.

This procedure was also carried out on a normal testicular cDNA library, using a 1:200 serum dilution.

A total of $1.12 \times 10^6$ pfus were screened in the breast cancer cDNA library, and 38 positive clones were identified. With respect to the testicular library, $4 \times 10^5$ pfus were screened, and 28 positive clones were identified.

Additionally, $8 \times 10^5$ pfus from the BR11 cDNA library were screened using the pooled serum described. Of these, 23 were positive.

The positive clones were subcloned, purified, and excised to forms suitable for insertion in plasmids. Following amplification of the plasmids, DNA inserts were evaluated via restriction mapping (EcoRI-XbaI), and clones which represented different cDNA inserts were sequenced using standard methodologies.

If sequences were identical to sequences found in GenBank, they were classified as known genes, while sequences which shared identity only with ESTs, or were identical to nothing in these data bases, were designated as unknown genes. Of the clones from the breast cancer library which were positive with autologous serum, 3 were unknown genes. Of the remaining 35, 15 were identical to either NY-ESO-1, or SSX2, two known members of the CT antigen family described supra, while the remaining clones corresponded to 14 known genes. Of the testicular library, 12 of the clones were SSX2.

The NY-ESO-1 antigen was not found, probably because the commercial library that was used had been size fractionated to have an average length of 1.5 kilobases, which is larger than full length NY-ESO-1 cDNA which is about 750 base pairs long.

With respect to the screening carried out with pooled, allogeneic sera, four of the clones were NY-ESO-1. No other CT antigens were identified. With the exception of NY-ESO-1, all of the genes identified were expressed universally in normal tissue.

A full listing of the isolated genes, and their frequency of occurrence follows, in tables 1, 2 and 3. Two genes were found in both the BR11 and testicular libraries, i.e., poly (ADP-ribose) polymerase, and tumor suppression gene ING1. The poly (ADP-ribose) polymerase gene has also been found in colon cancer libraries screened via SEREX, as is disclosed by Scanlan, et al., Int. J. Cancer 76: 652-58 (1998) when the genes identified in the screening of the BR11 cDNA library by autologous and allogeneic sera were compared, NY-ESO-1 and human keratin.

TABLE 1

SEREX-defined genes identified by autologous screening of BR11 cDNA library

| Gene group | No. of clones | Comments | Expression |
|---|---|---|---|
| CT genes | 10 | NY-ESO-1 | tumor, testis |
| | 5 | SSX2 | tumor, testis |
| Non-CT genes | 5 | Nuclear Receptor Co-Repressor | ubiquitous |
| | 4 | Poly(ADP-ribose) polymerase | ubiquitous |
| | 2 | Adenylosuccinatelyase | ubiquitous |
| | 2 | cosmid 313 (human) | ESTs: muscle, brain, breast |
| | 1 | CD 151 (transmembrane protein) | ubiquitous |
| | 1 | Human HRY Gen | RT-PCR: multiple normal tissues |
| | 1 | Alanyl-t-RNA-Synthetase | ubiquitous |
| | 1 | NAD(+) ADP-Ribosyltransferase | unbiquitous |
| | 1 | Human keratin 10 | ESTs: multiple normal tissues |
| | 1 | Human EGFR. kinase substrate | ubiquitous |
| | 1 | ING I Tumor suppressor gene | RT-PCR: multiple normal tissues |
| | 1 | Unknown gene, NCI_CGAP_Prl2 cDNA clone | ESTs: pancreas, liver, spleen, uterus |
| | 1 | Unknown gene | ESTs: multiple normal tissues |
| | 1 | Unknown gene | RT-PCR: multiple normal tissues |

TABLE 2

SEREX-defined genes identified by allogeneic screening of BR11 cDNA library

| Gene group | No. of clones | Comments | Expression |
|---|---|---|---|
| CT genes | 4 | NY-ESO-1 | tumor, testis |
| Non-CT genes | 6 | zinc-finger helicase | ESTs: brain, fetal heart, total fetus |
| | 4 | Acetoacetyl-CoA-thiolase | ubiquitous |
| | 3 | KIAA0330 gene | ESTs: multiple normal tissues |
| | 2 | U1snRNP | ubiquitous |
| | 1 | Human aldolase A | ubiquitous |
| | 1 | Retinoblastoma binding protein 6 | ESTs: tonsils, fetal brain, endothelial cells, brain |
| | 1 | α2-Macroglobulin receptor associated protein | ubiquitous |
| | 1 | Human Keratin 10 | ESTs: multiple normal tissues |

TABLE 3

SEREX-defined genes identified by screening of a testicular cDNA library with BR11 serum

| Gene group | No. of clones | Comments | Expression |
|---|---|---|---|
| CT genes: | 12 | SSX2 | tumor, testis |
| Non-CT genes: | 3 | Rho-associated coiled-coil forming protein | ubiquitous |
| | 3 | Poly(ADP-ribose) polymerase | ubiquitous |
| | 3 | Gene from HeLa cell, similar to TITIN | ubiquitous |
| | 2 | Gene from parathyroid tumor | RT-PCR: multiple normal tissues |
| | 1 | Transcription termination factor I-interacting peptide 21 | ubiquitous |
| | 1 | Gene from fetal heart | ESTs: multiple normal tissues |
| | 1 | ING 1 tumor suppressor gene | RT-PCR: multiple normal tissues |
| | 1 | KIAA0647 cDNA | ESTs: multiple normal tissues |
| | 1 | KIAA0667 cDNA | ESTs: multiple normal tissues |

EXAMPLE 2

The mRNA expression pattern of the cDNAs identified in example 1, in both normal and malignant tissues, was studied. To do this, gene specific oligonucleotide primers were designed which would amplify cDNA segments 300-600 base pairs in length, using a primer melting temperature of 65-70° C. The primers used for amplifying MAGE-1,2,3 and 4 BAGE, NY-ESO-1, SCP1 and SSX1, 2, 3, 4 and 5 were known primers, or were based on published sequences. See Chen, et al. supra; Tureci, et al., Proc. Natl. Acad. Sci. USA 95: 5211-16 (1998). Güre, et al., Int. J. Cancer 72: 965-71 (1997); Chen, et al., Proc. Natl. Acad. Sci. USA 91: 1004-1008 (1994); Gaugler, et al., J. Exp. Med. 179: 921-930 (1994), dePlaen, et al., Immunogenetics 40: 360-369 (1994), all of which are incorporated by reference. RT-PCR was carried out for 35 amplification cycles, at an annealing temperature of 60° C. Using this RT-PCR assay, the breast cancer tumor specimen was positive for a broad range of CT antigens, including MAGE-1,3 AND 4, BAGE, SSX2, NY-ESO-1 and CT7. The known CT antigens SCP-1, SSX1, 4 and 5 were not found to be expressed.

An additional set of experiments were carried out, in which the seroreactivity of patient sera against tumor antigens was tested. Specially, ELISAs were carried out, in accordance with Stockert, et al., J. Exp. Med. 187: 1349-1354 (1998), incorporated by reference, to determine if antibodies were present in the patient sera. Assays were run for MAGE-1, MAGE-3, NY-ESO-1, and SSX2. The ELISAs were positive for NY-ESO-1 and SSX2, but not the two MAGE antigens.

EXAMPLE 3

Two clones (one from the breast cancer cDNA library and one from the testicular library), were identified as a gene referred to as ING1, which is a tumor suppressor gene candidate. See Garkavtsev, et al., Nature 391: 295-8 (1998), incorporated by reference. The sequence found in the breast cancer library, differed from the known sequence of ING1 at six residues, i.e., positions 818, 836, 855, 861, 866 and 874. The sequence with the six variants is set forth at SEQ ID NO: 1. The sequence of wild type ING1 is set out at SEQ ID NO: 2.

To determine if any of these differences represented a mutation in tumors, a short, PCR fragment which contained the six positions referred to supra was amplified from a panel of allogeneic normal tissue, subcloned, amplified, and sequenced following standard methods.

The results indicated that the sequences in the allogeneic tissues were identical to what was found in tumors, ruling out the hypothesis that the sequence differences were a tumor associated mutation. This conclusion was confirmed, using the testicular library clone, and using restriction analysis of ING1 cDNA taken from normal tissues. One must conclude, therefore, that the sequence information provided by Garkavtsev, et al., supra, is correct.

EXAMPLE 4

Additional experiments were carried out to determine whether genetic variations might exist in the 5' portion of the ING1 gene, which might differ from the 5' portion of the clone discussed supra (SEQ ID NO: 1). In a first group of experiments, attempts were made to obtain full length ING1 cDNA from both the breast tumor library, and the testicular library. SEQ ID NO: 1 was used as a probe of the library, using standard methods.

Four clones were isolated from the testicular library and none were isolated from the breast cancer library. The four clones, following sequencing, were found to derive from three transcript variants. The three variants were identical from position 586 down to their 3' end, but differed in their 5' regions, suggesting alternatively spliced variants, involving the same exon-intron junction. All three differed from the sequence of ING1 described by Garkavtsev, et al., in Nat. Genet. 14: 415-420 (1996). These three variants are set out as SEQ ID NOS: 1, 3 and 4.

All of the sequences were then analyzed. The ORFs of SEQ ID NOS: 2, 1 and 4 (SEQ ID NO: 2 is the originally disclosed, ING1 sequence), encode polypeptides of 294, 279 and 235 amino acids, of which 233 are encoded by the 3' region common to the three sequences. These putative sequences are set out as SEQ ID NOS: 19, 5, and 7. With respect to SEQ ID NO: 3, however, no translational initiation site could be identified in its 5' region.

EXAMPLE 5

The data regarding SEQ ID NO: 3, described supra, suggested further experiments to find additional ORFs in the 5-end of variant transcripts of the molecule. In order to determine this, 5'-RACE-PCR was carried out using gene specific and adapted specific primers, together with commercially available products, and standard methodologies.

The primers used for these experiments were:

```
CACACAGGATCCATGTTGAGTCCTGCCAACGGCGTGGTCGTGGTTGCTGG

ACGCG
```

(SEQ ID NOS: 9 and 10), for SEQ ID NO: 1;

```
CCCAGCGGCCCTGACGCTGTCCGTGGTCGTGGTTGCTGGACGCG
```

(SEQ ID NOS: 11 and 12), for SEQ ID NO: 3; and

```
GGAAGAGATAAGGCCTAGGGAAGCGTGGTCGTGGTTGCTGGACGCG
```

(SEQ ID NOS: 13 and 14), for SEQ ID NO: 4.

Cloning and sequencing of the products of RACE PCR showed that the variant sequence of SEQ ID NO: 4 was 5' to SEQ ID NO: 3, and that full length cDNA for the variant SEQ ID NO: 3 contained an additional exon 609 nucleotides long, positioned between SEQ ID NO: 3 and the shared, 3' sequence referred to supra. This exon did not include an ORF. The first available initiation site would be an initial methionine at amino acid 70 of SEQ ID NO: 1. Thus, if expressed, SEQ ID NO: 3 would correspond to a molecule with a 681 base pair, untranslated 5' end and a region encoding 210 amino acids (SEQ ID NO: 6).

EXAMPLE 6

The presence of transcript variants with at least 3 different trancriptional initiation sites, and possibly different promoters, suggested that mRNA expression might be under different, tissue specific regulation.

To determine this, variant-specific primers were synthesized, and RT-PCR was carried out on a panel of tissues, using standard methods.

SEQ ID NO: 1 was found to be expressed universally in all of the normal breast, brain and testis tissues examined, in six breast cancer lines, and 8 melanoma cell lines, and in cultured melanocytes. SEQ ID NO: 3 was found to be expressed in four of the six breast cancer lines, normal testis, liver, kidney, colon and brain. SEQ ID NO: 4 was only found to be expressed by normal testis cells and weakly in brain cells.

EXAMPLE 7

A further set of experiments were carried out to determine if antibodies against ING1 were present in sera of normal and cancer patients. A phase plaque immuno assay of the type described supra was carried out, using clones of SEQ ID NO: 1 as target. Of 14 allogeneic sera taken from breast cancer patients, two were positive at 1:200 dilutions. All normal sera were negative.

EXAMPLE 8

The BR11 cDNA library described supra was then screened, using SEQ ID NO: 1 and standard methodologies. A 593 base pair cDNA was identified, which was different from any sequences in the data banks consulted. The sequence of this cDNA molecule is set out at SEQ ID NO: 8.

The cDNA molecule set forth as SEQ ID NO: 1 was then used in Southern blotting experiments. In brief, genomic DNA was isolated from normal human tissue, digested with BamHI or Hind III, and then separated onto 0.7% agarose gel, blotted onto nitrocellulose filters, and hybridized using $^{32}P$ labelled SEQ ID NO: 1, at high stringency conditions (aqueous buffer, 65° C.). The probes were permitted to hybridize overnight, and then exposed for autoradiography. Two hybridizing DNA species were identified, i.e., SEQ ID NOS: 1 and 8.

EXAMPLE 9

The cDNA molecule set forth in SEQ ID NO: 8 was then analyzed. 5'-RACE PCR was carried out using normal fetus cDNA. Full length cDNA for the molecule is 771 base pairs long, without the poly A tail. It shows strong homology to SEQ ID NO: 1, with the strongest homology in the 5' two-thirds (76% identity over nucleotide 1-480); however, the longest ORF is only 129 base pairs, and would encode a poly peptide 42 amino acids long which was homologous to, but much shorter than, the expected expression product of SEQ ID NO: 1.

In addition to the coding region, SEQ ID NO: 8 contains 203 base pairs of 5'-untranslated region, and 439 base pairs of 3'-untranslated region.

RT-PCR assays were carried out, as described supra. All of the normal tissues tested, including brain, colon, testis, tissue and breast, were positive for expression of this gene. Eight melanoma cell lines were tested, of which seven showed varying levels of expression, and one showed no expression. Six breast cancer cell lines were tested, of which four showed various levels of expression, and two showed no expression.

EXAMPLE 10

An additional breast cancer cDNA library, referred to as "BR17-128", was screened, using autologous sera. A cDNA molecule was identified.

Analysis of the sequence suggested that it was incomplete at the 5' end. To extend the sequence, a testicular cDNA library was screened with a nucleotide probe based upon the partial sequence identified in the breast cancer library. An additional 1200 base pairs were identified following these screenings. The 2011 base pairs of information are set forth in SEQ ID NO: 15.

The longest open reading frame is 1539 base pairs, corresponding to a protein of about 59.15 kilodaltons. The deduced sequence is set forth at SEQ ID NO: 16.

RT-PCR was then carried out using the following primers:

CACACAGGATCCATGCAGGCCCCGCACAAGGAGCACACAAAGCTTCTAGG

ATTTGGCACAGCCAGAG (SEQ ID NOS: 17 and 18)

Strong signals were observed in normal testis and breast tissue, and weak expression was observed in placenta.

No expression was found in normal brain, kidney, liver, colon, adrenal, fetal brain, lung, pancreas, prostate, thymus, uterus, and ovary tissue of tumor cell lines tested, 2 of the breast cancer lines were strongly positive and two were weakly positive. Of melanoma two of 8 were strongly positive, and 3 were weakly positive. Of lung cancer cell lines, 4 of 15 were strongly positive, and 3 were weakly positive.

When cancer tissue specimens were tested, 16 of 25 breast cancer samples were strongly positive, and 3 additional samples were weakly positive. Two of 36 melanoma samples were positive (one strong, one weak). All other cancer tissue samples were negative.

When Northern blotting was carried out, a high molecular weight smear was observed in testis, but in no other tissues tested.

EXAMPLE 11

Further experiments were carried out using the tumor sample referred to in example 10, supra. This sample was derived from a subcutaneous metastasis of a 60 year old female breast cancer patient. Total RNA was extracted, as described supra. Following the extraction, a cDNA library was constructed in K-ZAP expression vectors, also as described supra. Screening was carried out using the protocol set forth in example 1. A total of $7 \times 10^5$ pfus were screened. Fourteen reactive clones were identified, purified, and sequenced. The sequences were then compared to published sequences in GenBank and EST databases. These analyses indicated that the clones were derived from seven distinct genes, two of which were known, and five unknown. The two known genes were "PBK-1" (three clones), and TI-227 (one clone). These are universally expressed genes, with the libraries referred to supra showing ESTs for these genes from many different tissues.

With respect to the remaining 10 clones, six were derived from the same gene, referred to hereafter as "NY-BR-1." Three cDNA sequences were found in the EST database which shared identity with the gene. Two of these (AI 951118 and AW 373574) were identified as being derived from a breast cancer library, while the third (AW 170035), was from a pooled tissue source.

EXAMPLE 12

The distribution of the new gene NY-BR-1 referred to supra was determined via RT-PCR. In brief, gene specific oligonucleotide NY-BR-1 primers were designed to amplify cDNA segments 300-600 base pairs in length, with primer melting temperatures estimated at 65-70° C. The RT-PCR was then carried out over 30 amplification cycles, using a thermal cycler, and an annealing temperature of 60° C. Products were analyzed via 1.5% gel electrophoresis, and ethidium bromide visualization. Fifteen normal tissues (adrenal gland, fetal brain, lung, mammary gland, pancreas, placenta, prostate, thymus, uterus, ovary, brain, kidney, liver, colon and testis) were assayed. The NY-BR-1 clone gave a strong signal in mammary gland and testis tissue, and a very faint signal in placenta. All other tissues were negative. The other clones were expressed universally, based upon comparison to information in the EST database library, and were not pursued further.

The expression pattern of NY-BR-1 in cancer samples was then tested, by carrying out RT-PCR, as described supra, on tumor samples.

In order to determine the expression pattern, primers:

```
caaagcagag cctcccgaga ag      (SEQ ID NO: 20)

and cctatgctgc tcttcgattc ttcc    (SEQ ID NO: 21)
``` were used.

Of twenty-five breast cancer samples tested, twenty two were positive for NY-BR-1. Of these, seventeen gave strong signals, and five gave weak to modest signals.

An additional 82 non-mammary tumor samples were also analyzed, divided into 36 melanoma, 26 non small cell lung cancer, 6 colon cancer, 6 squamous cell carcinoma, 6 transitional cell carcinoma, and two leiyomyosarcomas. Only two melanoma samples were positive for NY-BR-1 expression.

The study was then extended to expression of NY-BR-1 in tissue culture. Cell lines derived from breast tumor, melanoma, and small cell lung cancer were studied. Four of six breast cancer cells were positive (two were very weak), four of eight melanoma (two very weak), and seven of fourteen small cell lung cancer lines (two very weak) were positive.

EXAMPLE 13

In order to determine the complete cDNA molecule for NY-BR-1, the sequences of the six clones referred to supra were compiled, to produce a nucleotide sequence 1464 base pairs long. Analysis of the open reading frame showed a continuous ORF throughout, indicating that the compiled sequence is not complete.

Comparison of the compiled sequence with the three EST library sequences referred to supra allowed for extension of the sequence. The EST entry AW170035 (446 base pairs long) overlapped the compiled sequence by 89 base pairs at its 5' end, permitting extension of the sequence by another 357 base pairs. A translational terminal codon was identified in this way, leading to a molecule with a 3'-untranslated region 333 base pairs long. The 5' end of the molecule was lacking, however, which led to the experiment described infra.

EXAMPLE 14

In order to determine the missing, 5' end of the clone described supra, a commercially available testis cDNA expression library was screened, using a PCR expression product of the type described supra as a probe. In brief, $5 \times 10^4$ pfus per 150 mm plate were transferred to nitrocellulose membranes, which were then submerged in denaturation solution (1.5M NaCl and 0.5 M NaOH), transferred to neutralization solution (1.5 M NaCl and 0.5M Tris-HCl), and then rinsed with 0.2M Tris-HCl, and 2×SSC. Probes were labelled with $^{32}P$ and hybridization was carried out at high stringency conditions (i.e., 68° C., aqueous buffer). Any positive clones were subcloned, purified, and in vivo excised to plasmid PBK-CMV, as described supra.

One of the clones identified in this way included an additional 1346 base pairs at the 5' end; however, it was not a full length molecule. A 5'-RACE-PCR was carried out, using commercially available products. The PCR product was cloned into plasmid vector pGEMT and sequenced. The results indicated that cDNA sequence was extended 1292 base pairs further, but no translation initiation site could be determined, because no stop codons could be detected. It could be concluded, however, that the cDNA of the NY-BR17 clone comprises at least 4026 nucleotides, which are presented as SEQ ID NO: 22. The molecule, as depicted, encodes a protein at least about 152.8 kDA in molecular weight. Structurally, there are 99 base pairs 5' to the presumed translation initiation site, and an untranslated segment 333 base pairs long at the 3' end. The predicted amino acid sequence of the coding region for SEQ ID NO: 22 is set out at SEQ ID NO: 23.

SEQ ID NO: 23 was analyzed for motifs, using the known search programs PROSITE and Pfam. A bipartite nuclear localization signal motif was identified at amino acids 17-34, suggesting that the protein is a nuclear protein. Five tandem ankyrin repeats were identified, at amino acids 49-81, 82-114, 115-147, 148-180 and 181-213. A bZIP site (i.e., a DNA binding site followed by a leucine zipper motif) was found at amino acid positions 1077-1104, suggesting a transcription factor function. It was also observed that three repetitive elements were identified in between the ankyrin repeats and the bZIP DNA binding site. To elaborate, a repetitive element 117 nucleotides long is trandemly repeated 3 times, between amino acids 459-815. The second repetitive sequence, consisting of 11 amino acids, repeats 7 times between amino acids 224 and 300. The third repetitive element, 34 amino acids long, is repeated twice, between amino acids 301-368.

EXAMPLE 15

The six clones described supra were compared, and analysis revealed that they were derived from two different splice variants. Specifically, two clones, referred to as "BR17-8" and "BR 17-44a", contain one more exon, of 111 base pairs (nucleotides 3015-3125 of SEQ ID NO: 22), which encodes amino acids 973-1009 of SEQ ID NO: 23, than do clones BR 17-1a, BR17-35b and BR17-44b. The shortest of the six clones, BR17-128, starts 3' to the additional exons. The key structural elements referred to supra were present in both splice variants, suggesting that there was no difference in biological function.

The expression pattern of the two splice variants was assessed via PT-PCR, using primers which spanned the 111 base pair exon referred to supra.

The primers used were:

```
aatgggaaca agagctctgc ag    (SEQ ID NO: 24)

and gggtcatctg aagttcagca ttc   (SEQ ID NO: 25)
```

Both variants were expressed strongly in normal testis and breast. The longer variant was dominant in testis, and the shorter variant in breast cells. When breast cancer cells were tested, co-typing of the variant was observed, (7 strongly, 2 weakly positive, and 1 negative), with the shorter variant being the predominant form consistently.

EXAMPLE 16

The frequency of antibody response against NY-BR-1 in breast cancer patients was tested. To do this, a recombinant protein consisting of amino acids 993-1188 of SEQ ID NO: 23 was prepared. (This is the protein encoded by clone BR 17-128, referred to supra). A total of 140 serum samples were taken from breast cancer patients, as were 60 normal serum samples. These were analyzed via Western blotting, using standard methods.

Four of the cancer sera samples were positive, including a sample from patient BR17. All normal sera were negative.

An additional set of experiments was then carried out to determine if sera recognized the portion of NY-BR-1 protein with repetitive elements. To do this, a different recombinant protein, consisting of amino acids 405-1000 was made, and tested in Western blot assays. None of the four antibody positive sera reacted with this protein indicating that an antibody epitope is located in the non-repetitive, carboxy terminal end of the molecule.

EXAMPLE 17

The screening of the testicular cDNA library referred to supra resulted, inter alia, in the identification of a cDNA molecule that was homologous to NY-BR-1. The molecule is 3673 base pairs in length, excluding the poly A tail. This corresponded to nucleotides 1-3481 of SEQ ID NO: 22, and showed 62% homology thereto. No sequence identity to sequences in libraries was noted. ORF analysis identified an ORF from nucleotide 641 through the end of the sequence, with 54% homology to the protein sequence of SEQ ID NO: 23. The ATG initiation codon of this sequence is 292 base pairs further 3' to the presumed initiation codon of NY-BR-1, and is preceded by 640 untranslated base pairs at its 5' end. This 640 base pair sequence includes scattered stop codons. The nucleotide sequence and deduced amino acid sequence are presented as SEQ ID NOS: 26 and 27, respectively.

RT-PCR analysis was carried out in the same way as is described supra, using primers:

```
tct catagat gctggtgctg atc      (SEQ ID NO: 28)

and cccagacatt gaattttggc agac.     (SEQ ID NO: 29)
```

Tissue restricted mRNA expression was found. The expression pattern differed from that of SEQ ID NO: 22. In brief, of six normal tissues examined, strong signals were found in brain and testis only. There was no or weak expression in normal breast tissues, and kidney, liver and colon tissues were negative. Eight of ten 10 breast cancer specimens tested supra were positive for SEQ ID NO: 26. Six samples were positive for both SEQ ID NO: 22 and 26, one for SEQ ID NO: 22 only, two for the SEQ ID NO: 26 only, and one was negative for both.

EXAMPLE 18

Recently, a working draft of the human genome sequence was released. This database was searched, using standard methods, and NY-BR-1 was found to have sequence identity with at least three chromosome 10 clones, identified by Genbank accession numbers AL157387, AL37148, and AC067744. These localize NY-BR-1 to chromosome 10 p11.21-12.1.

The comparison of NY-BR-1 and the human genomic sequence led to definition of NY-BR-1 exon-intron organization. In brief, the coding region of the gene contains essentially 19 structurally distinct exons with at least 2 exons encoding 3' untranslated regions. Detailed exon-intron junction information is described at Genbank AF 269081.

The six ankyrin repeats, referred to supra, are all found within exon 7. The 357 nucleotide repeating unit is composed of exons 10-15. The available genomic sequences are not complete, however, and only one of the three copies was identified, suggesting that DNA sequences between exons 5 and 10 may be duplicated and inserted in tandem, during genetic evolution. In brief, when the isolated NY-BR-1 cDNA clone was analyzed, three complete and one incomplete copy of the repeating units are present. The exon sequences can be expresses as exons 1-2-3-4-5-6-7-8-9-(10-11-12-13-14-15)-(10A-11A-12A-13A-14A-15A)-(10B-11B-12B-13B-14B-15B)-(10C-11C-12C-13C-14C)-16-17-18-19-20-21, wherein A, B & C are inexact copies of exon 10-15 sequences. Cloned, NY-BR-1 cDNA has 38 exons in toto.

It was noted, supra, that the sequence of NY-BR-1 cDNA was not complete at the 5' end. Genonic sequence (Genbank AC067744), permitted extension of the 5' end. Translation of the 5' genonic sequence led to the identification of a new translation initiation site, 168 base pairs upstream of the previously predicted ATG initiation codon. This led to an NY-BR-1 polypeptide including 1397 amino acid longer, 56 residue of which are added at the N-terminus, compared to prior sequence information, i.e.:

```
                                         (SEQ ID NO: 30)
MEEISAAAVKVVPGPERPSPFSQLVYTSNDSYIVHSGDLRKIHKAASRGQ

VRKLEK.
```

EXAMPLE 20

Reference was made, supra, to the two difference splice variants of NY-BR-1. Comparison of the splice variants with the genomic sequence confirmed that an alternate splicing event, with the longer variant incorporating part of intron 33 into exon 34 (i.e., exon 17 of the basic exon/intron framework described supra).

Key structural elements that were predicted in NY-BR-1, described supra, are present in both variants, suggesting that there is no difference in biological function, or subcellular location.

EXAMPLE 21

As with NY BR-1, the variant NY-BR-1.1, described supra, was screened against the working draft of the human genome sequence. One clone was found with sequence identity, i.e., GenBank AL359312, derive from chromosome 9. Thus, NY-BR-1 and NY-BR-1.1 both appear to be functioning genes, on two different chromosomes. The Genbank sequence referred to herein does not contain all of NY-BR-1.1, which precludes defining exon-intron structure. Nonetheless, at least 3 exons can be defined, which correspond to exons 16-18 of the NY-BR-1 basic framework. Exon-intron junctions are conserved.

EXAMPLE 22

A series of peptides were synthesized, based upon the amino acid sequence of NY-BR-1, as set forth in SEQ ID NO: 23. These were then tested for their ability to bind to HLA-A2 molecules and to stimulate CTL proliferation, using an ELISPOT assay. This assay involved coating 96-well, flat bottom nitrocellulose plates with 5 ug/ml of anti-interferon gamma antibodies in 100 ul of PBS per well, followed by overnight incubation. Purified $CD8^+$ cells, which had been separated from PBL samples via magnetic beads coated with anti-CD8 antibodies were then added, at $1 \times 10^5$ cells/well, in RPMI 1640 medium, that had been supplemented with 10% human serum, L-asparagine (50 mg/l), L-arginine (242 mg/l), L-glutamine (300 mg/l), together with IL-2 (2.5 ng/ml), in a final volume of 100 ul. $CD8^+$ effector cells were prepared by presensitizing with peptide, and were then added at from $5 \times 10^3$ to $2 \times 10^4$ cells/well. Peptides were pulsed onto irradiated T2 cells at a concentration of 10 ug/ml for 1 hour, washed and added to effector cells, at $5 \times 10^4$ cells/well. The plates were incubated for 16 hours at 37° C., washed six times with 0.05% Tween 20/PBS, and were then supplemented with biotinylated, anti-interferon gamma specific antibody at 0.5 ug/ml. After incubation for 2 hours at 37° C., plates were washed, and developed with commercially available reagents, for 1 hour, followed by 10 minutes of incubation with dye substrate. Plates were then prepped for counting, positives being indicated by blue spots. The number of blue spots/well was determined as the frequency of NY-ESO-1 specific CTLs/well.

Experiments were run, in triplicate, and total number of CTLs was calculated. As controls, one of reagents alone, effector cells alone, or antigen presenting cells alone were used. The difference between the number of positives in stimulated versus non-stimulated cells, was calculated as the effective number of peptide specific CTLs above background. Three peptides were found to be reactive, i.e.:

LLSHGAVIEV
(amino acids 102-111 of SEQ ID NO: 23)

SLSKILDTV
(amino acids 904-912 of SEQ ID NO: 23)

SLDQKLFQL
(amino acids 1262-1270 of SEQ ID NO: 23).

The complete list of peptides tested, with reference to their position in SEQ ID NO: 23, follows:

| Peptide | Position |
|---|---|
| FLVDRKVCQL | 35-43 of SEQ ID NO: 23 |
| ILIDSGADI | 68-76 of SEQ ID NO: 23 |
| AVYSEILSV | 90-98 of SEQ ID NO: 23 |
| ILSVVAKLL | 95-103 of SEQ ID NO: 23 |
| LLSHGAVIEV | 102-111 of SEQ ID NO: 23 |
| KLLSHGAVI | 101-109 of SEQ ID NO: 23 |
| FLLIKNANA | 134-142 of SEQ ID NO: 23 |
| MLLQQNVDV | 167-175 of SEQ ID NO: 23 |
| GMLLQQNVDV | 166-175 of SEQ ID NO: 23 |
| LLQQNVDVFA | 168-177 of SEQ ID NO: 23 |
| IAWEKKETPV | 361-370 of SEQ ID NO: 23 |
| SLFESSAKI | 430-438 of SEQ ID NO: 23 |
| CIPENSIYQKV | 441-450 of SEQ ID NO: 23 |
| KVMEINREV | 449-457 of SEQ ID NO: 23 |
| ELMDMQTFKA | 687-696 of SEQ ID NO: 23 |
| ELMDMQTFKA | 806-815 of SEQ ID NO: 23 |
| SLSKILDTV | 904-912 of SEQ ID NO: 23 |
| KILDTVHSC | 907-915 of SEQ ID NO: 23 |
| ILNEKIREEL | 987-996 of SEQ ID NO: 23 |
| RIQDIELKSV | 1018-1027 of SEQ ID NO: 23 |
| YLLHENCML | 1043-1051 of SEQ ID NO: 23 |
| CMLKKEIAML | 1049-1058 of SEQ ID NO: 23 |
| AMLKLELATL | 1056-1065 of SEQ ID NO: 23 |
| KILKEKNAEL | 1081-1090 of SEQ ID NO: 23 |
| VLIAENTML | 1114-1122 of SEQ ID NO: 23 |
| CLQRKMNVDV | 1174-1183 of SEQ ID NO: 23 |
| KMNVDVSST | 1178-1186 of SEQ ID NO: 23 |
| SLDQKLFQL | 1262-1270 of SEQ ID NO: 23 |
| KLFQLQSKNM | 1266-1275 of SEQ ID NO: 23 |
| FQLQSKNMWL | 1268-1277 of SEQ ID NO: 23 |
| QLQSKNMWL | 1269-1277 of SEQ ID NO: 23 |
| NMWLQQQLV | 1274-1282 of SEQ ID NO: 23 |
| WLQQQLVHA | 1276-1284 of SEQ ID NO: 23 |
| KITIDIIFL | 1293-1301 of SEQ ID NO: 23 |

The foregoing examples describe the isolation of a nucleic acid molecule which encodes a cancer associated antigen. "Associated" is used herein because while it is clear that the relevant molecule was expressed by several types of cancer, other cancers, not screened herein, may also express the antigen.

The invention relates to nucleic acid molecules which encode the antigens encoded by, e.g., SEQ ID NOS: 1, 3, 8, 15, 22 and 26 as well as the antigens encoded thereby, such as the proteins with the amino acid sequences of SEQ ID NOS: 5, 6, 7, 16, 23, 27, and 30. It is to be understood that all sequences which encode the recited antigen are a part of the invention.

Also a part of the invention are proteins, polypeptides, and peptides, which comprise, e.g., at least nine consecutive amino acids found in SEQ ID NO: 23, or at least nine consecutive amino acids of the amino acids of SEQ ID NO: 30. Proteins, polypeptides and peptides comprising nine or more amino acids of SEQ ID NO: 5, 6, 7, 16 or 27 are also a part of the invention. Especially preferred are peptides comprising or consisting of amino acids 102-111, 904-912, or 1262-1270 of SEQ ID NO: 23. Such peptides may, but do not necessarily provoke CTL responses when complexed with an HLA molecule, such as an HLA-A2 molecule. They may also bind to different MHC or HLA molecules, including, but not being limited to, HLA-A1, A2, A3, B7, B8, Cw3, Cw6, or serve, e.g., as immunogens, as part of immunogenic cocktail compositions, where they are combined with other proteins or polypeptides, and so forth. Also a part of the invention are the nucleic acid molecules which encode these molecules, such as "minigenes," expression vectors that include the coding regions, recombinant cells containing these, and so forth. All are a part of the invention.

Also a part of the invention are expression vectors which incorporate the nucleic acid molecules of the invention, in operable linkage (i.e., "operably linked") to a promoter. Construction of such vectors, such as viral (e.g., adenovirus or Vaccinia virus) or attenuated viral vectors is well within the skill of the art, as is the transformation or transfection of cells, to produce eukaryotic cell lines, or prokaryotic cell strains which encode the molecule of interest. Exemplary of the host cells which can be employed in this fashion are COS cells, CHO cells, yeast cells, insect cells (e.g., *Spodoptera frugiperda*), NIH 3T3 cells, and so forth. Prokaryotic cells, such as *E. coli* and other bacteria may also be used. Any of these cells can also be transformed or transfected with further nucleic acid molecules, such as those encoding cytokines, e.g., interleukins such as IL-2, 4, 6, or 12 or HLA or MHC molecules.

Also a part of the invention are the antigens described herein, both in original form and in any different post translational modified forms. The molecules are large enough to be antigenic without any posttranslational modification, and hence are useful as immunogens, when combined with an adjuvant (or without it), in both precursor and post-translationally modified forms. Antibodies produced using these antigens, both poly and monoclonal, are also a part of the invention as well as hybridomas which make monoclonal antibodies to the antigens. The whole protein can be used therapeutically, or in portions, as discussed infra. Also a part of the invention are antibodies against this antigen, be these polyclonal, monoclonal, reactive fragments, such as Fab, (F(ab)₂' and other fragments, as well as chimeras, humanized antibodies, recombinantly produced antibodies, and so forth.

As is clear from the disclosure, one may use the proteins and nucleic acid molecules of the invention diagnostically. The SEREX methodology discussed herein is premised on an immune response to a pathology associated antigen. Hence, one may assay for the relevant pathology via, e.g., testing a body fluid sample of a subject, such as serum, for reactivity with the antigen per se. Reactivity would be deemed indicative of possible presence of the pathology. So, too, could one assay for the expression of any of the antigens via any of the standard nucleic acid hybridization assays which are well known to the art, and need not be elaborated upon herein. One could assay for antibodies against the subject molecules, using standard immunoassays as well.

Analysis of SEQ ID NO: 1, 3, 4, 8, 15, 22 and 26 will show that there are 5' and 3' non-coding regions presented therein. The invention relates to those isolated nucleic acid molecules which contain at least the coding segment, and which may contain any or all of the non-coding 5' and 3' portions.

Also a part of the invention are portions of the relevant nucleic acid molecules which can be used, for example, as oligonucleotide primers and/or probes, such as one or more of SEQ ID NOS: 9, 10, 11, 12, 13, 14, 17, 18, 20, 21, 24, 25, 28, and 29 as well as amplification products like nucleic acid molecules comprising at least nucleotides 305-748 of SEQ ID NO: 1, or amplification products described in the examples, including those in examples 12, 14, etc.

As was discussed supra, study of other members of the "CT" family reveals that these are also processed to peptides which provoke lysis by cytolytic T cells. There has been a great deal of work on motifs for various MHC or HLA molecules, which is applicable here. Hence, a further aspect of the invention is a therapeutic method, wherein one or more peptides derived from the antigens of the invention which bind to an HLA molecule on the surface of a patient's tumor cells are administered to the patient, in an amount sufficient for the peptides to bind to the MHC/HLA molecules, and provoke lysis by T cells. Any combination of peptides may be used. These peptides, which may be used alone or in combination, as well as the entire protein or immunoreactive portions thereof, may be administered to a subject in need thereof, using any of the standard types of administration, such as intravenous, intradermal, subcutaneous, oral, rectal, and transdermal administration. Standard pharmaceutical carriers, adjuvants, such as saponins, GM-CSF, and interleukins and so forth may also be used. Further, these peptides and proteins may be formulated into vaccines with the listed material, as may dendritic cells, or other cells which present relevant MHC/peptide complexes.

Similarly, the invention contemplates therapies wherein nucleic acid molecules which encode the proteins of the invention, one or more or peptides which are derived from these proteins are incorporated into a vector, such as a Vaccinia or adenovirus based vector, to render it transfectable into eukaryotic cells, such as human cells. Similarly, nucleic acid molecules which encode one or more of the peptides may be incorporated into these vectors, which are then the major constituent of nucleic acid bases therapies.

Any of these assays can also be used in progression/regression studies. One can monitor the course of abnormality involving expression of these antigens simply by monitoring levels of the protein, its expression, antibodies against it and so forth using any or all of the methods set forth supra.

It should be clear that these methodologies may also be used to track the efficacy of a therapeutic regime. Essentially, one can take a baseline value for a protein of interest using any of the assays discussed supra, administer a given therapeutic agent, and then monitor levels of the protein thereafter, observing changes in antigen levels as indicia of the efficacy of the regime.

As was indicated supra, the invention involves, inter alia, the recognition of an "integrated" immune response to the molecules of the invention. One ramification of this is the ability to monitor the course of cancer therapy. In this method, which is a part of the invention, a subject in need of the therapy receives a vaccination of a type described herein. Such a vaccination results, e.g., in a T cell response against cells presenting HLA/peptide complexes on their cells. The response also includes an antibody response, possibly a result of the release of antibody provoking proteins via the lysis of cells by the T cells. Hence, one can monitor the effect of a vaccine, by monitoring an antibody response. As is indicated, supra, an increase in antibody titer may be taken as an indicia of progress with a vaccine, and vice versa. Hence, a further aspect of the invention is a method for monitoring efficacy of a vaccine, following administration thereof, by determining levels of antibodies in the subject which are specific for the vaccine itself, or a large molecule of which the vaccine is a part.

The identification of the subject proteins as being implicated in pathological conditions such as cancer also suggests a number of therapeutic approaches in addition to those discussed supra. The experiments set forth supra establish that antibodies are produced in response to expression of the protein. Hence, a further embodiment of the invention is the treatment of conditions which are characterized by aberrant or abnormal levels of one or more of the proteins, via administration of antibodies, such as humanized antibodies, antibody fragments, and so forth. These may be tagged or labelled with appropriate cystostatic or cytotoxic reagents.

T cells may also be administered. It is to be noted that the T cells may be elicited in vitro using immune responsive cells such as dendritic cells, lymphocytes, or any other immune responsive cells, and then reperfused into the subject being treated.

Note that the generation of T cells and/or antibodies can also be accomplished by administering cells, preferably treated to be rendered non-proliferative, which present relevant T cell or B cell epitopes for response, such as the epitopes discussed supra.

The therapeutic approaches may also include antisense therapies, wherein an antisense molecule, preferably from 10 to 100 nucleotides in length, is administered to the subject either "neat" or in a carrier, such as a liposome, to facilitate incorporation into a cell, followed by inhibition of expression of the protein. Such antisense sequences may also be incorporated into appropriate vaccines, such as in viral vectors (e.g., Vaccinia), bacterial constructs, such as variants of the known BCG vaccine, and so forth.

Other features and applications of the invention will be clear to the skilled artisan, and need not be set forth herein. The terms and expression which have been employed are used as terms of description and not of limitation, and there is no intention in the use of such terms and expression of excluding any equivalents of the features shown and described or portions thereof, it being recognized that various modifications are possible within the scope of the invention.

We claim:

1. An isolated nucleic acid molecule consisting of a nucleotide sequence which encodes the amino acid sequence of SEQ ID NO: 30.

2. An expression vector comprising the isolated nucleic acid molecule of claim 1, in operable linkage with a promoter.

3. The expression vector of claim 2, wherein said expression vector is a viral vector.

4. The expression vector of claim 3, wherein said viral vector is an Adenovirus or Vaccinia virus.

5. An isolated recombinant cell transformed or transfected with the isolated nucleic acid molecule of claim 1.

6. The isolated recombinant cell of claim 5, which is a eukaryotic cell.

7. The isolated recombinant cell of claim 5, which is a prokaryotic cell.

8. The isolated recombinant cell of claim 5, which is a COS cell, a CHO cell, a yeast cell, an insect cell, or an *E. coil* cell.

9. The isolated recombinant cell of claim 5, further transformed or transfected with a second nucleic acid molecule.

10. The isolated recombinant cell, claim 9, wherein said second nucleic acid molecule encodes for a cytokine, an HLA molecule or an MHC molecule.

* * * * *

SEQUENCE LISTING

<160> NUMBER OF SEQ ID NOS: 30

<210> SEQ ID NO 1
<211> LENGTH: 1533
<212> TYPE: DNA
<213> ORGANISM: Homo sapiens
<220> FEATURE:
<221> NAME/KEY: CDS
<222> LOCATION: 235
<223> OTHER INFORMATION: unknown nucleotide

<400> SEQUENCE: 1

| | | | | | |
|---|---|---|---|---|---|
| ggttttccac | gttggacaag | tgcggctcgg | cggccagcgg | agcgcgcccc | ttcccgctgc | 60
| ccgctccgct | cctctcttct | acccagccca | gtgggcgagt | gggcagcggc | ggccgcggcg | 120
| ctgggccctc | tcccgccggt | gtgtgcgcgc | tcgtacgcgc | ggcccccggc | gccagccccg | 180
| ccgcctgaga | gggggcctgc | gccgccggcc | ggggcgtgcg | cccggagcc | accgncaccg | 240
| cggcccgcgc | cctcaggcgc | tggggtcccc | gcggacccgg | aggcggcgga | cgggctcggc | 300
| agatgtagcc | gccgggccga | agcaggagcc | ggcggggggg | cgccgggaga | gcgagggctt | 360
| tgcattttgc | agtgctattt | tttgaggggg | gcggagggtg | gaggaagtcg | gaaagccgcg | 420
| ccgagtcgcc | ggggacctcc | ggggtgaacc | atgttgagtc | ctgccaacgg | ggagcagctc | 480
| cacctggtga | actatgtgga | ggactacctg | gactccatcg | agtccctgcc | tttcgacttg | 540
| cagagaaatg | tctcgctgat | gcgggagatc | gacgcgaaat | accaagagat | cctgaaggag | 600
| ctagacgagt | gctacgagcg | cttcagtcgc | gagacagacg | gggcgcagaa | gcggcggatg | 660
| ctgcactgtg | tgcagcgcgc | gctgatccgc | agccaggagc | tgggcgacga | gaagatccag | 720
| atcgtgagcc | agatggtgga | gctggtggag | aaccgcacgc | ggcaggtgga | cagccacgtg | 780
| gagctgttcg | aggcgcagca | ggagctgggc | gacacagcgg | gcaacagcgg | caaggctggc | 840
| gcggacaggc | ccaaaggcga | ggcggcagcg | caggctgaca | agcccaacag | caagcgctca | 900
| cggcggcagc | gcaacaacga | gaaccgtgag | aacgcgtcca | gcaaccacga | ccacgacgac | 960
| ggcgcctcgg | gcacacccaa | ggagaagaag | gccaagacct | ccaagaagaa | gaagcgctcc | 1020
| aaggccaagg | cggagcgaga | ggcgtcccct | gccgacctcc | ccatcgaccc | caacgaaccc | 1080
| acgtactgtc | tgtgcaacca | ggtctcctat | ggggagatga | tcggctgcga | caacgacgag | 1140
| tgccccatcg | agtggttcca | cttctcgtgc | gtggggctca | atcataaacc | caagggcaag | 1200
| tggtactgtc | ccaagtgccg | gggggagaac | gagaagacca | tggacaaagc | cctggagaaa | 1260
| tccaaaaaag | agagggctta | aacaggtag | tttgtggaca | ggcgcctggt | gtgaggagga | 1320
| caaaataaac | cgtgtattta | ttacattgct | gcctttgttg | aggtgcaagg | agtgtaaaat | 1380
| gtatattttt | aaagaatgtt | agaaaaggaa | ccattccttt | catagggatg | gcagtgattc | 1440
| tgtttgcctt | ttgttttcat | tggtacacgt | gtaacaagaa | agtggtctgt | ggatcagcat | 1500
| tttagaaact | acaaatatag | gtttgattca | aca | | | 1533

<210> SEQ ID NO 2
<211> LENGTH: 1143
<212> TYPE: DNA
<213> ORGANISM: Homo sapiens

<400> SEQUENCE: 2

| | | | | | |
|---|---|---|---|---|---|
| gagtaacccg | ataatatgcc | gttgtccggc | acggcgacga | gaattcccag | atatagcagt | 60
| agcagtgatc | ccgggcctgt | ggctcggggc | cggggctgca | gttcggaccg | cctcccgcga | 120

| | |
|---|---|
| cccgcggggg ctcggagaca gtttcaggcc gcatctttgc tgacccgagg gtggggccgc | 180 |
| gcgtggccgt ggaaacagat cctgaaggag ctagacgagt gctacgagcg cttcagtcgc | 240 |
| gagacagacg gggcgcagaa gcggcggatg ctgcactgtg tgcagcgcgc gctgatccgc | 300 |
| agccaggagc tgggcgacga gaagatccag atcgtgagcc agatggtgga gctggtggag | 360 |
| aaccgcacgc ggcaggtgga cagccacgtg gagctgttcg aggcgcagca ggagctgggc | 420 |
| gacacagtgg gcaacagcgg caaggttggc gcggacaggc ccaatggcga tgcggtagcg | 480 |
| cagtctgaca agcccaacag caagcgctca cggcggcagc gcaacaacga gaaccgtgag | 540 |
| aacgcgtcca gcaaccacga ccacgacgac ggcgcctcgg gcacacccaa ggagaagaag | 600 |
| gccaagacct ccaagaagaa gaagcgctcc aaggccaagg cggagcgaga ggcgtcccct | 660 |
| gccgacctcc ccatcgaccc caacgaaccc acgtactgtc tgtgcaacca ggtctcctat | 720 |
| ggggagatga tcggctgcga caacgacgag tgccccatcg agtggttcca cttctcgtgc | 780 |
| gtggggctca atcataaacc caagggcaag tggtactgtc ccaagtgccg ggggagaac | 840 |
| gagaagacca tggacaaagc cctggagaaa tccaaaaaag agagggctta acacaggtag | 900 |
| tttgtggaca ggcgcctggt gtgaggagga caaaataaac cgtgtattta ttacattgct | 960 |
| gcctttgttg aggtgcaagg agtgtaaaat gtatattttt aaagaatgtt agaaaaggaa | 1020 |
| ccattccttt catagggatg gcagtgattc tgtttgcctt ttgttttcat tggtacacgt | 1080 |
| gtaacaagaa agtggtctgt ggatcagcat tttagaaact acaaatatag gtttgattca | 1140 |
| aca | 1143 |

<210> SEQ ID NO 3
<211> LENGTH: 742
<212> TYPE: DNA
<213> ORGANISM: Homo sapiens

<400> SEQUENCE: 3

| | |
|---|---|
| cgccgtccac accccagcgg ccctgacgct gtccctccg cgaccctcgc ctctggaaaa | 60 |
| agtgacaggc aaggccacgc ccccgcgagg gccggcctcg agcccgcagc ccccagggcc | 120 |
| tgggacgaga tcctgaagga gctagacgag tgctacgagc gcttcagtcg cgagacagac | 180 |
| ggggcgcaga agcggcggat gctgcactgt gtgcagcgcg cgctgatccg cagccaggag | 240 |
| ctgggcgacg agaagatcca gatcgtgagc cagatggtgg agctggtgga gaaccgcacg | 300 |
| cggcaggtgg acagccacgt ggagctgttc gaggcgcagc aggagctggg cgacacagcg | 360 |
| ggcaacagcg gcaaggctgg cgcggacagg cccaaggcg aggcggcagc gcaggctgac | 420 |
| aagcccaaca gcaagcgctc acggcggcag cgcaacaacg agaaccgtga gaacgcgtcc | 480 |
| agcaaccacg accacgacga cggcgcctcg ggcacaccca aggagaagaa ggccaagacc | 540 |
| tccaagaaga gaagcgctc caaggccaag gcggagcgag aggcgtcccc tgccgacctc | 600 |
| cccatcgacc ccaacgaacc cacgtactgt ctgtgcaacc aggtctccta tggggagatg | 660 |
| atcggctgcg acaacgacga gtgccccatc gagtggttcc acttctcgtg cgtgggctc | 720 |
| aatcataaac ccaagggcaa gt | 742 |

<210> SEQ ID NO 4
<211> LENGTH: 857
<212> TYPE: DNA
<213> ORGANISM: Homo sapiens

<400> SEQUENCE: 4

```
cctccgagaa cggtgtccat ggcacagggc gggaagagat aaggcctagg gaaggcgccc    60
ctcgggccta tccacctctt ctggggctcg gcactaggaa gcagcttccc tctcaggccc   120
ctttgtctcc aagccgttcc aaactgagta ccgggagacg acacaaaggg agggcggtga   180
cggatggcgc aggcgcggga gccgcctagg ctgctgggag tggtggtccg gccgcggaat   240
ggagatcctg aaggagctag acgagtgcta cgagcgcttc agtcgcgaga cagacggggc   300
gcagaagcgg cggatgctgc actgtgtgca gcgcgcgctg atccgcagcc aggagctggg   360
cgacgagaag atccagatcg tgagccagat ggtggagctg gtggagaacc gcacgcggca   420
ggtggacagc cacgtggagc tgttcgaggc gcagcaggag ctgggcgaca cagcgggcaa   480
cagcggcaag gctggcgcgg acaggcccaa aggcgaggcg cagcgcagg ctgacaagcc   540
caacagcaag cgctcacggc ggcagcgcaa caacgagaac cgtgagaacg cgtccagcaa   600
ccacgaccac gacgacggcg cctcgggcac acccaaggag aagaaggcca agacctccaa   660
gaagaagaag cgctccaagg ccaaggcgga gcgagaggcg tcccctgccg acctccccat   720
cgaccccaac gaacccacgt actgtctgtg caaccaggtc tcctatgggg agatgatcgg   780
ctgcgacaac gacgagtgcc ccatcgagtg gttccacttc tcgtgcgtgg ggctcaatca   840
taaacccaag ggcaagt                                                   857

<210> SEQ ID NO 5
<211> LENGTH: 279
<212> TYPE: PRT
<213> ORGANISM: Homo sapiens

<400> SEQUENCE: 5

Met Leu Ser Pro Ala Asn Gly Glu Gln Leu His Leu Val Asn Tyr Val
1               5                   10                  15

Glu Asp Tyr Leu Asp Ser Ile Glu Ser Leu Pro Phe Asp Leu Gln Arg
            20                  25                  30

Asn Val Ser Leu Met Arg Glu Ile Asp Ala Lys Tyr Gln Glu Ile Leu
        35                  40                  45

Lys Glu Leu Asp Glu Cys Tyr Glu Arg Phe Ser Arg Glu Thr Asp Gly
    50                  55                  60

Ala Gln Lys Arg Arg Met Leu His Cys Val Gln Arg Ala Leu Ile Arg
65                  70                  75                  80

Ser Gln Glu Leu Gly Asp Glu Lys Ile Gln Ile Val Ser Gln Met Val
                85                  90                  95

Glu Leu Val Glu Asn Arg Thr Arg Gln Val Asp Ser His Val Glu Leu
            100                 105                 110

Phe Glu Ala Gln Gln Glu Leu Gly Asp Thr Val Gly Asn Ser Gly Lys
        115                 120                 125

Val Gly Ala Asp Arg Pro Asn Gly Asp Ala Val Ala Gln Ser Asp Lys
    130                 135                 140

Pro Asn Ser Lys Arg Ser Arg Arg Gln Arg Asn Asn Glu Asn Arg Glu
145                 150                 155                 160

Asn Ala Ser Ser Asn His Asp His Asp Asp Gly Ala Ser Gly Thr Pro
                165                 170                 175

Lys Glu Lys Lys Ala Lys Thr Ser Lys Lys Lys Arg Ser Lys Ala
            180                 185                 190

Lys Ala Glu Arg Glu Ala Ser Pro Ala Asp Leu Pro Ile Asp Pro Asn
        195                 200                 205

Glu Pro Thr Tyr Cys Leu Cys Asn Gln Val Ser Tyr Gly Glu Met Ile
    210                 215                 220
```

```
Gly Cys Asp Asn Asp Glu Cys Pro Ile Glu Trp Phe His Phe Ser Cys
225                 230                 235                 240

Val Gly Leu Asn His Lys Pro Lys Gly Lys Trp Tyr Cys Pro Lys Cys
                245                 250                 255

Arg Gly Glu Asn Glu Lys Thr Met Asp Lys Ala Leu Glu Lys Ser Lys
            260                 265                 270

Lys Glu Arg Ala Tyr Asn Arg
        275

<210> SEQ ID NO 6
<211> LENGTH: 210
<212> TYPE: PRT
<213> ORGANISM: Homo sapiens

<400> SEQUENCE: 6

Met Leu His Cys Val Gln Arg Ala Leu Ile Arg Ser Gln Glu Leu Gly
1               5                   10                  15

Asp Glu Lys Ile Gln Ile Val Ser Gln Met Val Glu Leu Val Glu Asn
            20                  25                  30

Arg Thr Arg Gln Val Asp Ser His Val Glu Leu Phe Glu Ala Gln Gln
        35                  40                  45

Glu Leu Gly Asp Thr Val Gly Asn Ser Gly Lys Val Gly Ala Asp Arg
    50                  55                  60

Pro Asn Gly Asp Ala Val Ala Gln Ser Asp Lys Pro Asn Ser Lys Arg
65                  70                  75                  80

Ser Arg Arg Gln Arg Asn Asn Glu Asn Arg Glu Asn Ala Ser Ser Asn
                85                  90                  95

His Asp His Asp Asp Gly Ala Ser Gly Thr Pro Lys Glu Lys Lys Ala
            100                 105                 110

Lys Thr Ser Lys Lys Lys Lys Arg Ser Lys Ala Lys Ala Glu Arg Glu
        115                 120                 125

Ala Ser Pro Ala Asp Leu Pro Ile Asp Pro Asn Glu Pro Thr Tyr Cys
    130                 135                 140

Leu Cys Asn Gln Val Ser Tyr Gly Glu Met Ile Gly Cys Asp Asn Asp
145                 150                 155                 160

Glu Cys Pro Ile Glu Trp Phe His Phe Ser Cys Val Gly Leu Asn His
                165                 170                 175

Lys Pro Lys Gly Lys Trp Tyr Cys Pro Lys Cys Arg Gly Glu Asn Glu
            180                 185                 190

Lys Thr Met Asp Lys Ala Leu Glu Lys Ser Lys Lys Glu Arg Ala Tyr
        195                 200                 205

Asn Arg
    210

<210> SEQ ID NO 7
<211> LENGTH: 235
<212> TYPE: PRT
<213> ORGANISM: Homo sapiens

<400> SEQUENCE: 7

Met Glu Ile Leu Lys Glu Leu Asp Glu Cys Tyr Glu Arg Phe Ser Arg
1               5                   10                  15

Glu Thr Asp Gly Ala Gln Lys Arg Arg Met Leu His Cys Val Gln Arg
            20                  25                  30

Ala Leu Ile Arg Ser Gln Glu Leu Gly Asp Glu Lys Ile Gln Ile Val
        35                  40                  45
```

-continued

```
Ser Gln Met Val Glu Leu Val Glu Asn Arg Thr Arg Gln Val Asp Ser
 50                  55                  60
His Val Glu Leu Phe Glu Ala Gln Gln Glu Leu Gly Asp Thr Val Gly
 65                  70                  75                  80
Asn Ser Gly Lys Val Gly Ala Asp Arg Pro Asn Gly Asp Ala Val Ala
                 85                  90                  95
Gln Ser Asp Lys Pro Asn Ser Lys Arg Ser Arg Gln Arg Asn Asn
            100                 105                 110
Glu Asn Arg Glu Asn Ala Ser Ser Asn His Asp His Asp Asp Gly Ala
            115                 120                 125
Ser Gly Thr Pro Lys Glu Lys Lys Ala Lys Thr Ser Lys Lys Lys Lys
    130                 135                 140
Arg Ser Lys Ala Lys Ala Glu Arg Glu Ala Ser Pro Ala Asp Leu Pro
145                 150                 155                 160
Ile Asp Pro Asn Glu Pro Thr Tyr Cys Leu Cys Asn Gln Val Ser Tyr
                165                 170                 175
Gly Glu Met Ile Gly Cys Asp Asn Asp Glu Cys Pro Ile Glu Trp Phe
            180                 185                 190
His Phe Ser Cys Val Gly Leu Asn His Lys Pro Lys Gly Lys Trp Tyr
        195                 200                 205
Cys Pro Lys Cys Arg Gly Glu Asn Glu Lys Thr Met Asp Lys Ala Leu
    210                 215                 220
Glu Lys Ser Lys Lys Glu Arg Ala Tyr Asn Arg
225                 230                 235
```

<210> SEQ ID NO 8
<211> LENGTH: 772
<212> TYPE: DNA
<213> ORGANISM: Homo sapiens
<220> FEATURE:
<221> NAME/KEY: CDS
<222> LOCATION: 689,714
<223> OTHER INFORMATION: unknown nucleotides

<400> SEQUENCE: 8

```
aaagcgttct cggcggcagc gcaacaacta gaaccgtgag aacgcgtcca gcaaccgcga      60
cccacgacga cgtcacctcg ggcacgccca aggagaagaa agcccagacc tctaagaaga     120
agcagggctc catggccaag gcgtagcggc aggcgtcccc cgcagacctc cccatcgacc     180
ccagcgagcc ctcctactgg gagatgatcc gctgcgacaa cgaatgcccc atcgagtggt     240
tccgcttctc gtgtgtgagt ctcaaccata accaaagcg caagtggtac tgttccagat      300
gccggggaaa gaacgatggg caaagccctt gagaagtcca gaaaaaaaac agggcttata     360
acaggtagtt tggggacatg cgtctaatag tgaggagaac aaaataagcc agtgtgttga     420
ttacattgcc acctttgctg aggtgcagga agtgtaaaat gtatatttt aaagaatgtt      480
gttagaggcc gggcgcggtg gctcacgcct gtaatcccag cactttggga ggccgaggcg     540
gtcggatcac gaggtcagga gatcgagacc atcctggcta acacggtgaa accccgtctc     600
tactaaaaat tcaaaaaaaa aattagctgg gcgtggtggc gggcgcctgt agtcccagct     660
attcgggagg ctgaggcagg agaatggcnt gaacctggga ggtggagctt gcantgagcc     720
aaggtcgcgc cactgcactc cagcctgggc gacagagcga gactccatct ta              772
```

<210> SEQ ID NO 9
<211> LENGTH: 32
<212> TYPE: DNA

<213> ORGANISM: Homo sapiens

<400> SEQUENCE: 9
cacacaggat ccatgttgag tcctgccaac gg                                        32

<210> SEQ ID NO 10
<211> LENGTH: 23
<212> TYPE: DNA
<213> ORGANISM: Homo sapiens

<400> SEQUENCE: 10
cgtggtcgtg gttgctggac gcg                                                  23

<210> SEQ ID NO 11
<211> LENGTH: 21
<212> TYPE: DNA
<213> ORGANISM: Homo sapiens

<400> SEQUENCE: 11
cccagcggcc ctgacgctgt c                                                    21

<210> SEQ ID NO 12
<211> LENGTH: 23
<212> TYPE: DNA
<213> ORGANISM: Homo sapiens

<400> SEQUENCE: 12
cgtggtcgtg gttgctggac gcg                                                  23

<210> SEQ ID NO 13
<211> LENGTH: 23
<212> TYPE: DNA
<213> ORGANISM: Homo sapiens

<400> SEQUENCE: 13
ggaagagata aggcctaggg aag                                                  23

<210> SEQ ID NO 14
<211> LENGTH: 23
<212> TYPE: DNA
<213> ORGANISM: Homo sapiens

<400> SEQUENCE: 14
cgtggtcgtg gttgctggac gcg                                                  23

<210> SEQ ID NO 15
<211> LENGTH: 2030
<212> TYPE: DNA
<213> ORGANISM: Homo sapiens
<220> FEATURE:
<221> NAME/KEY: CDS
<222> LOCATION: 1628, 1752, 1758, 1769, 1789, 1873, 1908, 1915, 1933,
      1970, 1976, 2022
<223> OTHER INFORMATION: unknown nucleotides

<400> SEQUENCE: 15
ctcgtgccgt taaagatggt cttctgaagg ctaactgcgg aatgaaagtt tctattccaa          60
ctaaagcctt agaattgatg gacatgcaaa ctttcaaagc agagcctccc gagaagccat         120
ctgccttcga gcctgccatt gaaatgcaaa agtctgttcc aaataaagcc ttggaattga         180
agaatgaaca acattgaga gcagatgaga tactccccatc agaatccaaa caaaaggact         240
atgaagaaag ttcttgggat tctgagagtc tctgtgagac tgtttcacag aaggatgtgt         300

-continued

```
gtttacccaa ggctacacat caaaaagaaa tagataaaat aaatggaaaa ttagaagagt      360
ctcctgataa tgatggtttt ctgaaggctc cctgcagaat gaaagtttct attccaacta      420
aagccttaga attgatggac atgcaaactt tcaaagcaga gcctcccgag aagccatctg      480
ccttcgagcc tgccattgaa atgcaaaagt ctgttccaaa taaagccttg gaattgaaga      540
atgaacaaac attgagagca gatcagatgt tcccttcaga atcaaaacaa agaaggttg       600 aagaaaattc ttgggattct gagagtctcc gtgagactgt tcacagaag gatgtgtgtg      660 tacccaaggc tacacatcaa aaagaaatgg ataaaataag tggaaaatta gaagattcaa      720
ctagcctatc aaaaatcttg gatacagttc attcttgtga aagagcaagg gaacttcaaa      780
aagatcactg tgaacaacgt acaggaaaaa tggaacaaat gaaaagaag ttttgtgtac       840 tgaaaaagaa actgtcagaa gcaaagaaa taaaatcaca gttagagaac caaaagtta        900 aatgggaaca agagctctgc agtgtgagat tgacttttaaa ccaagaagaa gagaagagaa     960
gaaatgccga tatattaaat gaaaaaatta gggaagaatt aggaagaatc gaagagcagc     1020
ataggaaaga gttagaagtg aaacaacaac ttgaacaggc tctcagaata caagatatag     1080
aattgaagag tgtagaaagt aatttgaatc aggtttctca cactcatgaa aatgaaaatt     1140
atctcttaca tgaaaattgc atgttgaaaa aggaaattgc catgctaaaa ctggaaatag     1200
ccacactgaa acaccaatac caggaaaagg aaaataaata ctttgaggac attaagattt     1260
taaaagaaaa gaatgctgaa cttcagatga ccctaaaact gaaagaggaa tcattaacta     1320
aaagggcatc tcaatatagt gggcagctta agttctgat agctgagaac acaatgctca      1380
cttctaaatt gaaggaaaaa caagacaaag aaatactaga ggcagaaatt gaatcacacc     1440
atcctagact ggcttctgct gtacaagacc atgatcaaat tgtgacatca agaaaaagtc     1500
aagaacctgc tttccacatt gcaggagatg cttgtttgca agaaaaatg aatgttgatg      1560 tgagtagtac cgatatataa caatgaggtg ctccatcaac cactttctga agctcaaagg     1620
aaatccanaa gcctaaaaat taatctcaat tatgcaggag atgctctaag agaaaataca     1680
ttggtttcag gaacatgcac aaagagacca acgtgaaaca cagtgtcaaa tgaaggaagc     1740
tgaacacatg tntcaaancg aacaagatna tgtgaacaaa cacactganc agcaggagtc     1800
tctagatcag aaattatttc aactacaaag caaaaatatg tggcttcaac agcaattagt     1860
tcatgcacat aangaaagct gacaacaaaa gcaagataac aattgatntt cattntcttg     1920
agaggaaaat gcncatcatc ttctaaaaga gaaaaatgag gagatatttn attacnataa     1980
ccatttaaaa aacccgtata tttcaatatg gaaaaaaaaa anaaaaaaaa                 2030
```

<210> SEQ ID NO 16
<211> LENGTH: 512
<212> TYPE: PRT
<213> ORGANISM: Homo sapiens

<400> SEQUENCE: 16

Met Lys Val Ser Ile Pro Thr Lys Ala Leu Glu Leu Met Asp Met Gln
1               5                   10                  15

Thr Phe Lys Ala Glu Pro Pro Glu Lys Pro Ser Ala Phe Glu Pro Ala
            20                  25                  30

Ile Glu Met Gln Lys Ser Val Pro Asn Lys Ala Leu Glu Leu Lys Asn
        35                  40                  45

Glu Gln Thr Leu Arg Ala Asp Glu Ile Leu Pro Ser Glu Ser Lys Gln
    50                  55                  60

Lys Asp Tyr Glu Glu Ser Ser Trp Asp Ser Glu Ser Leu Cys Glu Thr

-continued

```
                65                   70                  75                  80
Val Ser Gln Lys Asp Val Cys Leu Pro Lys Ala Thr His Gln Lys Glu
                    85                  90                  95
Ile Asp Lys Ile Asn Gly Lys Leu Glu Glu Ser Pro Asp Asn Asp Gly
                100                 105                 110
Phe Leu Lys Ala Pro Cys Arg Met Lys Val Ser Ile Pro Thr Lys Ala
                115                 120                 125
Leu Glu Leu Met Asp Met Gln Thr Phe Lys Ala Glu Pro Pro Glu Lys
                130                 135                 140
Pro Ser Ala Phe Glu Pro Ala Ile Glu Met Gln Lys Ser Val Pro Asn
145                 150                 155                 160
Lys Ala Leu Glu Leu Lys Asn Glu Gln Thr Leu Arg Ala Asp Gln Met
                165                 170                 175
Phe Pro Ser Glu Ser Lys Gln Lys Val Glu Glu Asn Ser Trp Asp
                180                 185                 190
Ser Glu Ser Leu Arg Glu Thr Val Ser Gln Lys Asp Val Cys Val Pro
                195                 200                 205
Lys Ala Thr His Gln Lys Glu Met Asp Lys Ile Ser Gly Lys Leu Glu
                210                 215                 220
Asp Ser Thr Ser Leu Ser Lys Ile Leu Asp Thr Val His Ser Cys Glu
225                 230                 235                 240
Arg Ala Arg Glu Leu Gln Lys Asp His Cys Glu Gln Arg Thr Gly Lys
                245                 250                 255
Met Glu Gln Met Lys Lys Phe Cys Val Leu Lys Lys Lys Leu Ser
                260                 265                 270
Glu Ala Lys Glu Ile Lys Ser Gln Leu Glu Asn Gln Lys Val Lys Trp
                275                 280                 285
Glu Gln Glu Leu Cys Ser Val Arg Leu Thr Leu Asn Gln Glu Glu Glu
                290                 295                 300
Lys Arg Arg Asn Ala Asp Ile Leu Asn Glu Lys Ile Arg Glu Glu Leu
305                 310                 315                 320
Gly Arg Ile Glu Glu Gln His Arg Lys Glu Leu Glu Val Lys Gln Gln
                325                 330                 335
Leu Glu Gln Ala Leu Arg Ile Gln Asp Ile Glu Leu Lys Ser Val Glu
                340                 345                 350
Ser Asn Leu Asn Gln Val Ser His Thr His Glu Asn Glu Asn Tyr Leu
                355                 360                 365
Leu His Glu Asn Cys Met Leu Lys Lys Glu Ile Ala Met Leu Lys Leu
                370                 375                 380
Glu Ile Ala Thr Leu Lys His Gln Tyr Gln Glu Lys Glu Asn Lys Tyr
385                 390                 395                 400
Phe Glu Asp Ile Lys Ile Leu Lys Glu Lys Asn Ala Glu Leu Gln Met
                405                 410                 415
Thr Leu Lys Leu Lys Glu Glu Ser Leu Thr Lys Arg Ala Ser Gln Tyr
                420                 425                 430
Ser Gly Gln Leu Lys Val Leu Ile Ala Glu Asn Thr Met Leu Thr Ser
                435                 440                 445
Lys Leu Lys Glu Lys Gln Asp Lys Glu Ile Leu Glu Ala Glu Ile Glu
                450                 455                 460
Ser His His Pro Arg Leu Ala Ser Ala Val Gln Asp His Asp Gln Ile
465                 470                 475                 480
Val Thr Ser Arg Lys Ser Gln Glu Pro Ala Phe His Ile Ala Gly Asp
                485                 490                 495
```

```
Ala Cys Leu Gln Arg Lys Met Asn Val Asp Val Ser Ser Thr Asp Ile
            500                 505                 510
```

<210> SEQ ID NO 17
<211> LENGTH: 33
<212> TYPE: DNA
<213> ORGANISM: Homo sapiens

<400> SEQUENCE: 17
cacacaggat ccatgcaggc cccgcacaag gag         33

<210> SEQ ID NO 18
<211> LENGTH: 34
<212> TYPE: DNA
<213> ORGANISM: Homo sapiens

<400> SEQUENCE: 18
cacacaaagc ttctaggatt tggcacagcc agag         34

<210> SEQ ID NO 19
<211> LENGTH: 294
<212> TYPE: PRT
<213> ORGANISM: Homo sapiens

<400> SEQUENCE: 19

```
Met Pro Leu Cys Thr Ala Thr Arg Ile Pro Arg Tyr Ser Ser Ser Ser
 1               5                  10                  15

Asp Pro Gly Pro Val Ala Arg Gly Arg Gly Cys Ser Ser Asp Arg Leu
            20                  25                  30

Pro Arg Pro Ala Gly Pro Ala Arg Arg Gln Phe Gln Ala Ala Ser Leu
        35                  40                  45

Leu Thr Arg Gly Trp Gly Arg Ala Trp Pro Trp Lys Gln Ile Leu Lys
    50                  55                  60

Glu Leu Asp Glu Cys Tyr Glu Arg Phe Ser Arg Glu Thr Asp Gly Ala
65                  70                  75                  80

Gln Lys Arg Arg Met Leu His Cys Val Gln Arg Ala Leu Ile Arg Ser
                85                  90                  95

Gln Glu Leu Gly Asp Glu Lys Ile Gln Ile Val Ser Gln Met Val Glu
            100                 105                 110

Leu Val Glu Asn Arg Thr Arg Gln Val Asp Ser His Val Glu Leu Phe
        115                 120                 125

Glu Ala Gln Gln Glu Leu Gly Asp Thr Val Gly Asn Ser Gly Lys Val
    130                 135                 140

Gly Ala Asp Arg Pro Asn Gly Asp Ala Val Ala Gln Ser Asp Lys Pro
145                 150                 155                 160

Asn Ser Lys Arg Ser Arg Arg Gln Arg Asn Asn Glu Asn Arg Glu Asn
                165                 170                 175

Ala Ser Ser Asn His Asp His Asp Asp Gly Ala Ser Gly Thr Pro Lys
            180                 185                 190

Glu Lys Lys Ala Lys Thr Ser Lys Lys Lys Arg Ser Lys Ala Lys
        195                 200                 205

Ala Glu Arg Glu Ala Ser Pro Ala Asp Leu Pro Ile Asp Pro Asn Glu
    210                 215                 220

Pro Thr Tyr Cys Leu Cys Asn Gln Val Ser Tyr Gly Glu Met Ile Gly
225                 230                 235                 240

Cys Asp Asn Asp Glu Cys Pro Ile Glu Trp Phe His Phe Ser Cys Val
                245                 250                 255
```

```
Gly Leu Asn His Lys Pro Lys Gly Lys Trp Tyr Cys Pro Lys Cys Arg
        260                 265                 270

Gly Glu Asn Glu Lys Thr Met Asp Lys Ala Leu Glu Lys Ser Lys Lys
        275                 280                 285

Glu Arg Ala Tyr Asn Arg
    290             294

<210> SEQ ID NO 20
<211> LENGTH: 22
<212> TYPE: DNA
<213> ORGANISM: Homo sapiens

<400> SEQUENCE: 20
caaagcagag cctcccgaga ag                                              22

<210> SEQ ID NO 21
<211> LENGTH: 24
<212> TYPE: DNA
<213> ORGANISM: Homo sapiens

<400> SEQUENCE: 21
cctatgctgc tcttcgattc ttcc                                            24

<210> SEQ ID NO 22
<211> LENGTH: 4115
<212> TYPE: DNA
<213> ORGANISM: Homo sapiens

<400> SEQUENCE: 22
ctagtctata cagcaacgac cctacatcgt cactctgggg tcttagaaag tccataaagc     60
tgcctcccgg acaagtccg  aagctggaga gatgacaaag ggaagaagac atcaacctta    120
atatacaaga gcccagaaga gactgctcta actgggcctg gtcaatggcc tgaggaagta    180
gtaacatttc ggtagacaga agtgccagct gacgtccttg tggcgaacac ggacacctct    240
gatgaaggct acaatgccca caggaggctt gcaaatatt tgatagattc ggtgccgata    300
taaatctcgt gatgtgtatg caacatggct tccattatgc gtttatagtg gattttgtca    360
gtggtggcaa actgctgtcc atggtgcagt atcgaagtgc caacaaggct gcctcacacc    420
acttttacta ccataacgaa agaagtgagc aattgtggaa ttttgctgat aaaaatgcaa    480
atgcgaatgc gttaataagt taaatgcaca ccctcatgct gctgtatgtc tggatcatca    540
gagatagttg catgcttctt agcaaaatgt gacgtctttg tgcagatata gtggagtaac    600
tgcagaacat atgctgttac tgtggatttc tcacattcat aacaaattat gaatatatac    660
gaaaattatc aaaaatcatc aaataccaat cagaaggaac tctgcaggaa acctgatgag    720
gctgcaccct ggcggaaaga cacctgacac gctgaaagct ggtggaaaaa cacctgatga    780
ggctgcaccc tggtggaaag acacctgaca ggctgaaagc tggtggaaaa acacctgatg    840
aggctgcatc ttggtggagg aacatctgac aaattcaatg ttggagaaag gacatctgga    900
aagttcgaac gtcagcagaa aaacacctag gaaattacga tcctgcaaaa aaacatctga    960
gaaatttacg ggccagcaaa ggaagaccta agatcgcag ggagaaaaa gaagacacac     1020
ctagggaaat atgagtcccg aaaagaaaca ctgagaaatt acgtgggcag aaaaggaaga   1080
cctaggaaga cgcatgggag aaaagaaac cctgtaaaga tggatgcgtg caagagtaac   1140
atctaataaa ctaaagtttt gaaaaggaa atctaagatg ttgcatgtcc acaaaagaat   1200
catctacaaa gcaagtgcca tgatcagagg tcccatcaga tccaaacaag ggaagatgaa   1260
```

```
gaatattctt tgattctcgg gtctctttga agttctgcaa gattcaagtg gtatacctga   1320
gtctatatat aaaaagtaat gagataaata agaagtagaa agcctcctaa aagccatctg   1380
ccttcaagcc gccattgaaa gcaaaactct ttccaaataa gcctttgaat gaagaatgaa   1440
caaacattga agcagatccg tgttcccacc gaatccaaac aaaggactat aagaaaattc   1500
ttgggattct agagtctctg gagactgttt acagaaggat tgtgtttacc aaggctacac   1560
atcaaaaaga atagataaaa aaatggaaaa tagaagagtc cctaataaag tggtcttctg   1620
aaggctacct cggaatgaaa tttctattcc actaaagcct agaattgaag acatgcaaac   1680
tttcaaagcg agcctccggg aagccatctg cttcgagcct ccactgaaat caaaagtctg   1740
tcccaaataa gccttggaat gaaaaatgaa aaacatggag gcagatgaga actcccatca   1800
gaatccaaac aaaggactat aagaaaattc tgggatactg gagtctctgt agactgtttc   1860
acagaaggat tgtgtttacc aaggctgcgc tcaaaaagaa tagataaaat aatggaaaat   1920
tagaagggtc cctgttaaag tggtcttctg aggctaactg ggaatgaaag ttctattcca   1980
actaaagcct agaattgatg acatgcaaac ttcaaagcag gcctcccgag agccatctgc   2040
cttcgagcct ccattgaaat caaaagtctg tccaaataaa ccttggaatt aagaatgaac   2100
aaacattgag gcagatgaga actcccatca aatccaaaca aaggactatg agaaagttct   2160
tgggattctg gagtctctgt agactgtttc cagaaggatg gtgtttaccc aggctacaca   2220
tcaaaaagaa tagataaaat aatggaaaat agaagagtct ctgataatga ggttttctga   2280
aggctccctg agaatgaaag ttctattcca ctaaagcctt gaattgatgg catgcaaact   2340
ttcaaagcag gcctcccgag agccatctgc ttcgagcctg cattgaaatg aaaagtctgt   2400
tccaaataaa ccttggaatt aagaatgaac aacattgaga cagatcagat ttcccttcag   2460
aatcaaaaca agaaggttg agaaaattct gggattctga agtctccgtg gactgtttca   2520
cagaaggatg gtgtgtaccc aggctacaca caaaaagaaa ggataaaata gtggaaaatt   2580
agaagattca ctagcctatc aaaatcttgg tacagttcat cttgtgaaag gcaagggaac   2640
ttcaaaaaga cactgtgaac acgtacagga aaatggaaca atgaaaaaga gttttgtgta   2700
ctgaaaaaga actgtcagaa caaagaaat aaatcacagt agagaaccaa agttaaatg    2760 ggaacaagag tctgcagtgt agattgactt aaaccaagaa aagagaagag agaaatgccg   2820
atatattaaa gaaaaaatta ggaagaatta gaagaatcga gagcagcata gaaagagtta   2880
gaagtgaaac acaacttgaa aggctctcag atacaagata agaattgaag gtgtagaaag   2940
taatttgaat aggtttctca actcatgaaa tgaaaattat tcttacatga aattgcatgt   3000 tgaaaagga attgccatgc aaaactggaa tagccacact aaacaccaat ccaggaaaag    3060 gaaataaat ctttgaggac ttaagatttt aagaaaaga tgctgaactt agatgaccct     3120
aaaactgaaa aggaatcatt actaaaaggg atctcaatat gtgggcagct aaagttctga   3180
tagctgagaa acaatgctca ttctaaattg aggaaaaaca gacaaagaaa actagaggca   3240
gaaattgaat acaccatcct gactggcttc gctgtacaag ccatgatcaa ttgtgacatc   3300
aagaaaaagt aagaacctgc ttccacattg aggagatgct gtttgcaaag aaaatgaatg   3360
ttgatgtgag agtacgatat taacaatgag tgctccatca ccactttctg agctcaaagg   3420
aaatccaaaa cctaaaaatt atctcaatta gcaggagatg tctaagagaa atacattggt   3480
ttcagaacat cacaaagaga caacgtgaaa acagtgtcaa tgaaggaagc gaacacatgt   3540
atcaaaacga caagataatg gaacaaacac ctgaacagca gagtctctag tcagaaatta   3600
```

-continued

```
tttcaactac aagcaaaaat tgtggcttca cagcaattag tcatgcacat agaaagctga    3660
caacaaaagc agataacaat gatattcatt tcttgagagg aaatgcaaca catctcctaa    3720
aagagaaaaa gaggagatat taattacaat accatttaaa aaccgtatat tcaatatgaa    3780
aaagagaaag agaaacagaa actcatgaga acaagcagta gaaacttctt tggagaaaca    3840
acagaccaga ctttactcac actcatgcta gaggccagtc tagcatcacc tatgttgaaa    3900
atcttaccaa agtctgtgtc acagaatact attttagaag aaaattcatg tttcttcctg    3960
aagcctacag cataaaataa agtgtgaaga ttacttgttc cgaattgcat aagctgcaca    4020
ggattcccat taccctgatg tgcagcagac tcattcaatc aaccagaatc cgctctgcac    4080
tccagcctag tgacagagtg gactccacct ggaaa                              4115
```

<210> SEQ ID NO 23
<211> LENGTH: 1341
<212> TYPE: PRT
<213> ORGANISM: Homo sapiens

<400> SEQUENCE: 23

```
Met Thr Lys Arg Lys Thr Ile Asn Leu Asn Ile Gln Asp Ala Gln
1               5                   10                  15

Lys Arg Thr Ala Leu His Trp Ala Cys Val Asn Gly His Glu Glu Val
            20                  25                  30

Val Thr Phe Leu Val Asp Arg Lys Cys Gln Leu Asp Val Leu Asp Gly
        35                  40                  45

Glu His Arg Thr Pro Leu Met Lys Ala Leu Gln Cys His Gln Glu Ala
    50                  55                  60

Cys Ala Asn Ile Leu Ile Asp Ser Gly Ala Asp Ile Asn Leu Val Asp
65                  70                  75                  80

Val Tyr Gly Asn Met Ala Leu His Tyr Ala Val Tyr Ser Glu Ile Leu
                85                  90                  95

Ser Val Val Ala Lys Leu Leu Ser His Gly Ala Val Ile Glu Val His
            100                 105                 110

Asn Lys Ala Ser Leu Thr Pro Leu Leu Leu Ser Ile Thr Lys Arg Ser
        115                 120                 125

Glu Gln Ile Val Glu Phe Leu Leu Ile Lys Asn Ala Asn Ala Asn Ala
    130                 135                 140

Val Asn Lys Tyr Lys Cys Thr Ala Leu Met Leu Ala Val Cys His Gly
145                 150                 155                 160

Ser Ser Glu Ile Val Gly Met Leu Leu Gln Gln Asn Val Asp Val Phe
                165                 170                 175

Ala Ala Asp Ile Cys Gly Val Thr Ala Glu His Tyr Ala Val Thr Cys
            180                 185                 190

Gly Phe His His Ile His Glu Gln Ile Met Glu Tyr Ile Arg Lys Leu
        195                 200                 205

Ser Lys Asn His Gln Asn Thr Asn Pro Glu Gly Thr Ser Ala Gly Thr
    210                 215                 220

Pro Asp Glu Ala Ala Pro Leu Ala Glu Arg Thr Pro Asp Thr Ala Glu
225                 230                 235                 240

Ser Leu Val Glu Lys Thr Pro Asp Glu Ala Ala Pro Leu Val Glu Arg
                245                 250                 255

Thr Pro Asp Thr Ala Glu Ser Leu Val Glu Lys Thr Pro Asp Glu Ala
            260                 265                 270

Ala Ser Leu Val Glu Gly Thr Ser Asp Lys Ile Gln Cys Leu Glu Lys
        275                 280                 285
```

```
Ala Thr Ser Gly Lys Phe Glu Gln Ser Ala Glu Thr Pro Arg Glu
    290                 295                 300

Ile Thr Ser Pro Ala Lys Glu Thr Ser Glu Lys Phe Thr Trp Pro Ala
305                 310                 315                 320

Lys Gly Arg Pro Arg Lys Ile Ala Trp Glu Lys Lys Glu Asp Thr Pro
                325                 330                 335

Arg Glu Ile Met Ser Pro Ala Lys Glu Thr Ser Glu Lys Phe Thr Trp
            340                 345                 350

Ala Ala Lys Gly Arg Pro Arg Lys Ile Ala Trp Glu Lys Lys Glu Thr
        355                 360                 365

Pro Val Lys Thr Gly Cys Val Ala Arg Val Thr Ser Asn Lys Thr Lys
    370                 375                 380

Val Leu Glu Lys Gly Arg Ser Lys Met Ile Ala Cys Pro Thr Lys Glu
385                 390                 395                 400

Ser Ser Thr Lys Ala Ser Ala Asn Asp Gln Arg Phe Pro Ser Glu Ser
                405                 410                 415

Lys Gln Glu Glu Asp Glu Glu Tyr Ser Cys Asp Ser Arg Ser Leu Phe
            420                 425                 430

Glu Ser Ser Ala Lys Ile Gln Val Cys Ile Pro Glu Ser Ile Tyr Gln
        435                 440                 445

Lys Val Met Glu Ile Asn Arg Glu Val Glu Glu Pro Pro Lys Lys Pro
    450                 455                 460

Ser Ala Phe Lys Pro Ala Ile Glu Met Gln Asn Ser Val Pro Asn Lys
465                 470                 475                 480

Ala Phe Glu Leu Lys Asn Glu Gln Thr Leu Arg Ala Asp Pro Met Phe
                485                 490                 495

Pro Pro Glu Ser Lys Gln Lys Asp Tyr Glu Glu Asn Ser Trp Asp Ser
            500                 505                 510

Glu Ser Leu Cys Glu Thr Val Ser Gln Lys Asp Val Cys Leu Pro Lys
        515                 520                 525

Ala Thr His Gln Lys Glu Ile Asp Lys Ile Asn Gly Lys Leu Glu Glu
    530                 535                 540

Ser Pro Asn Lys Asp Gly Leu Leu Lys Ala Thr Cys Gly Met Lys Val
545                 550                 555                 560

Ser Ile Pro Thr Lys Ala Leu Glu Leu Lys Asp Met Gln Thr Phe Lys
                565                 570                 575

Ala Glu Pro Pro Gly Lys Pro Ser Ala Phe Glu Pro Ala Thr Glu Met
            580                 585                 590

Gln Lys Ser Val Pro Asn Lys Ala Leu Glu Leu Lys Asn Glu Gln Thr
        595                 600                 605

Trp Arg Ala Asp Glu Ile Leu Pro Ser Glu Ser Lys Gln Lys Asp Tyr
    610                 615                 620

Glu Glu Asn Ser Trp Asp Thr Glu Ser Leu Cys Glu Thr Val Ser Gln
625                 630                 635                 640

Lys Asp Val Cys Leu Pro Lys Ala Ala His Gln Lys Glu Ile Asp Lys
                645                 650                 655

Ile Asn Gly Lys Leu Glu Gly Ser Pro Val Lys Asp Gly Leu Leu Lys
            660                 665                 670

Ala Asn Cys Gly Met Lys Val Ser Ile Pro Thr Lys Ala Leu Glu Leu
        675                 680                 685

Met Asp Met Gln Thr Phe Lys Ala Glu Pro Pro Glu Lys Pro Ser Ala
    690                 695                 700
```

-continued

```
Phe Glu Pro Ala Ile Glu Met Gln Lys Ser Val Pro Asn Lys Ala Leu
705                 710                 715                 720

Glu Leu Lys Asn Glu Gln Thr Leu Arg Ala Asp Glu Ile Leu Pro Ser
            725                 730                 735

Glu Ser Lys Gln Lys Asp Tyr Glu Glu Ser Ser Trp Asp Ser Glu Ser
        740                 745                 750

Leu Cys Glu Thr Val Ser Gln Lys Asp Val Cys Leu Pro Lys Ala Thr
    755                 760                 765

His Gln Lys Glu Ile Asp Lys Ile Asn Gly Lys Leu Glu Glu Ser Pro
770                 775                 780

Asp Asn Asp Gly Phe Leu Lys Ala Pro Cys Arg Met Lys Val Ser Ile
785                 790                 795                 800

Pro Thr Lys Ala Leu Glu Leu Met Asp Met Gln Thr Phe Lys Ala Glu
            805                 810                 815

Pro Pro Glu Lys Pro Ser Ala Phe Glu Pro Ala Ile Glu Met Gln Lys
        820                 825                 830

Ser Val Pro Asn Lys Ala Leu Glu Leu Lys Asn Glu Gln Thr Leu Arg
    835                 840                 845

Ala Asp Gln Met Phe Pro Ser Glu Ser Lys Gln Lys Val Glu Glu
850                 855                 860

Asn Ser Trp Asp Ser Glu Ser Leu Arg Glu Thr Val Ser Gln Lys Asp
865                 870                 875                 880

Val Cys Val Pro Lys Ala Thr His Gln Lys Glu Met Asp Lys Ile Ser
            885                 890                 895

Gly Lys Leu Glu Asp Ser Thr Ser Leu Ser Lys Ile Leu Asp Thr Val
        900                 905                 910

His Ser Cys Glu Arg Ala Arg Glu Leu Gln Lys Asp His Cys Glu Gln
    915                 920                 925

Arg Thr Gly Lys Met Glu Gln Met Lys Lys Phe Cys Val Leu Lys
930                 935                 940

Lys Lys Leu Ser Glu Ala Lys Glu Ile Lys Ser Gln Leu Glu Asn Gln
945                 950                 955                 960

Lys Val Lys Trp Glu Gln Glu Leu Cys Ser Val Arg Leu Thr Leu Asn
            965                 970                 975

Gln Glu Glu Glu Lys Arg Arg Asn Ala Asp Ile Leu Asn Glu Lys Ile
        980                 985                 990

Arg Glu Glu Leu Gly Arg Ile Glu Glu Gln His Arg Lys Glu Leu Glu
    995                 1000                1005

Val Lys Gln Gln Leu Glu Gln Ala Leu Arg Ile Gln Asp Ile Glu Leu
    1010                1015                1020

Lys Ser Val Glu Ser Asn Leu Asn Gln Val Ser His Thr His Glu Asn
1025                1030                1035                1040

Glu Asn Tyr Leu Leu His Glu Asn Cys Met Leu Lys Lys Glu Ile Ala
            1045                1050                1055

Met Leu Lys Leu Glu Ile Ala Thr Leu Lys His Gln Tyr Gln Glu Lys
        1060                1065                1070

Glu Asn Lys Tyr Phe Glu Asp Ile Lys Ile Leu Lys Glu Lys Asn Ala
    1075                1080                1085

Glu Leu Gln Met Thr Leu Lys Leu Lys Glu Glu Ser Leu Thr Lys Arg
    1090                1095                1100

Ala Ser Gln Tyr Ser Gly Gln Leu Lys Val Leu Ile Ala Glu Asn Thr
1105                1110                1115                1120

Met Leu Thr Ser Lys Leu Lys Glu Lys Gln Asp Lys Glu Ile Leu Glu
```

-continued

```
                    1125                1130                1135
Ala Glu Ile Glu Ser His His Pro Arg Leu Ala Ser Ala Val Gln Asp
        1140                1145                1150

His Asp Gln Ile Val Thr Ser Arg Lys Ser Gln Glu Pro Ala Phe His
        1155                1160                1165

Ile Ala Gly Asp Ala Cys Leu Gln Arg Lys Met Asn Val Asp Val Ser
        1170                1175                1180

Ser Thr Ile Tyr Asn Asn Glu Val Leu His Gln Pro Leu Ser Glu Ala
1185                1190                1195                1200

Gln Arg Lys Ser Lys Ser Leu Lys Ile Asn Leu Asn Tyr Ala Gly Asp
        1205                1210                1215

Ala Leu Arg Glu Asn Thr Leu Val Ser Glu His Ala Gln Arg Asp Gln
        1220                1225                1230

Arg Glu Thr Gln Cys Gln Met Lys Glu Ala Glu His Met Tyr Gln Asn
        1235                1240                1245

Glu Gln Asp Asn Val Asn Lys His Thr Glu Gln Gln Glu Ser Leu Asp
        1250                1255                1260

Gln Lys Leu Phe Gln Leu Gln Ser Lys Asn Met Trp Leu Gln Gln
1265                1270                1275                1280

Leu Val His Ala His Lys Lys Ala Asp Asn Lys Ser Lys Ile Thr Ile
        1285                1290                1295

Asp Ile His Phe Leu Glu Arg Lys Met Gln His His Leu Leu Lys Glu
        1300                1305                1310

Lys Asn Glu Glu Ile Phe Asn Tyr Asn Asn His Leu Lys Asn Arg Ile
        1315                1320                1325

Tyr Gln Tyr Glu Lys Gly Lys Ala Glu Thr Glu Asn Ser
        1330                1335                1340

<210> SEQ ID NO 24
<211> LENGTH: 22
<212> TYPE: DNA
<213> ORGANISM: Homo sapiens

<400> SEQUENCE: 24
aatgggaaca agagctctgc ag                                              22

<210> SEQ ID NO 25
<211> LENGTH: 23
<212> TYPE: DNA
<213> ORGANISM: Homo sapiens

<400> SEQUENCE: 25
gggtcatctg aagttcagca ttc                                             23

<210> SEQ ID NO 26
<211> LENGTH: 3673
<212> TYPE: DNA
<213> ORGANISM: Homo sapiens
<220> FEATURE:
<221> NAME/KEY: CDS
<222> LOCATION: 439, 473, 1789
<223> OTHER INFORMATION: unknown nucleotides

<400> SEQUENCE: 26
caagagcttg gcgatacaga aatttctgct ggtgttgggg cgggtgcggg aactgaagac      60
gggcgagtgc gagccggggg cgggtgctgg ggaagggtaa gcggaagcg agggcgaggg      120 gtaggggctg gggaagggcg agcgggaggc gcgggctctc tctagcaggg ggctgcagcc     180
```

```
atgaagaggc tcttagctgc cgctggcaag ggcgtgcggg gcccggagcc cccgaacccc    240
ttcagcgaac gggtctacac tgagaaggac tacgggacca tctacttcgg ggatctaggg    300
aagatccata cagctgcctc ccggggccaa gtccagaagc tggagaagat gacagtaggg    360
aagaagcccg tcaacctgaa caaaagagat atgaagaaga ggactgctct acactgggcc    420
tgtgtcaatg ccatgcana agtagtaaca tttctggtag acagaaagtg ccngcttaat    480
gtccttgatg gcgaagggag gacacctctg atgaaggctc tacaatgcga gagggaagct    540
ttgtgcaaat attctcatag atgctggtgc tgatctaaat tatgtagatg tgtatggcaa    600
cacggctctc cattatgccg tttatagtga gaatttatta atggtggcaa cactgctgtc    660
ctatggtgca gtcatcgagg tgcaaaacaa ggctagcctc acacccttt tactggccat     720 acagaaaaga agcaagcaaa ctgtggaatt tttactaaca aaaatgcaa atgcaaacgc     780 atttaatgag tctaaatgca cagccctcat gcttgccata tgtgaaggct catcagagat    840
agtcggcatg cttcttcagc aaaatgttga cgtctttgct gaagacatac atggaataac    900
tgcagaacgt tatgctgctg ctcgtggagt taattacatt catcaacaac ttttggaaca    960
tatacgaaaa ttacctaaaa atcctcaaaa taccaatcca gaaggaacat ctacaggaac   1020
acctgatgag gctgcaccct ggcggaaaag aacacctgac acggctgaaa gcttgctgga   1080
aaaaacacct gacgaggctg cacgcttggt ggagggaacg tctgccaaaa ttcaatgtct   1140
ggggaaagca acatctggaa agtttgaaca gtcaacagaa gaaacaccta ggaaaatttt   1200
gaggcctaca aagaaacat ctgagaaatt ttcatggcca gcaaaagaaa gatctaggaa    1260
gatcacatgg gaggaaaaag aaacatctgt aaagactgaa tgcgtggcag gagtaacacc   1320
taataaaact gaagttttgg aaaaaggaac atctaatatg attgcatgtc ctacaaaaga   1380
aacatctaca aaagcaagta caaatgtgga tgtgagttct gtagagccta tattcagtct   1440
ttttggcaca cggactattg aaaattcaca gtgtacaaaa gttgaggaag actttaatct   1500
tgctaccaag attatctcta agagtgctgc acagaattat acgtgtttac ctgatgctac   1560
atatcaaaaa gatatcaaaa caataaatca caaaatagaa gatcagatgt tcccatcaga   1620
atccaaacga gaggaagatg aagaatattc ttgggattct gggagtctct tgagagttc    1680 tgcaaagact caagtgtgta tacctgagtc tatgtatcag aaagtaatgg agataaatag   1740
agaagtagaa gagcttcctg agaagccatc tgccttcaag cctgccgtng aaatgcaaaa   1800
gactgttcca aataaagcct ttgaattgaa gaatgaacaa acattgagag cagctcagat   1860
gttcccatca gaatccaaac aaaaggacga tgaagaaaat tcttgggatt ctgagagtcc   1920
ctgtgagacg gtttcacaga aggatgtgta tttacccaaa gctacacatc aaaaagaatt   1980
cgatacctta agtggaaaat tagaagagtc tcctgttaaa gatggtcttc tgaagcctac   2040
ctgtggaagg aaagtttctc ttccaaataa agccttagaa ttaaaggaca gagaaacatt   2100
caaagcagag tctcctgata agatggtctc tctgaagcct acctgtggaa ggaaagtttc   2160
tcttccaaat aaagccttag aattaaagga cagagaaaca ctcaaagcag agtctcctga   2220
taatgatggt cttctgaagc ctacctgtgg aaggaaagtt tctcttccaa ataaagcttt   2280
agaattgaag gacagagaaa cattcaaagc agctcagatg ttcccatcag aatccaaaca   2340
aaaggatgat gaagaaaatt cttgggattt tgagagtttc cttgagactc tcttacagaa   2400
tgatgtgtgt ttacccaagg ctacacatca aaaagaattc gatacctaa gtggaaaatt   2460 agaagagtct cctgataaag atggtcttct gaagcctacc tgtggaatga aatttctct    2520 tccaaataaa gccttagaat tgaaggacag agaaacattc aaagcagagg atgtgagttc   2580
```

-continued

```
tgtagagtcc acattcagtc tttttggcaa accgactact gaaaattcac agtctacaaa    2640
agttgaggaa gactttaatc ttactaccaa ggagggagca acaagacag taactggaca    2700 acaggaacgt gatattggca ttattgaacg agctccacaa gatcaaacaa ataagatgcc    2760
cacatcagaa ttaggaagaa aagaagatac aaaatcaact tcagattctg agattatctc    2820
tgtgagtgat acacagaatt atgagtgttt acctgaggct acatatcaaa agaaataaa    2880 gacaacaaat ggcaaaatag aagagtctcc tgaaaagcct tctcactttg agcctgccac    2940
tgaaatgcaa aactctgttc caaataaagg cttagaatgg aagaataaac aaacattgag    3000
agcagattca actaccctat caaaaatctt ggatgcactt ccttcttgtg aaagaggaag    3060
ggaacttaaa aaagataact gtgaacaaat tacagcaaaa atggaacaaa tgaaaaataa    3120
gttttgtgta ctacaaaagg aactgtcaga agcgaaagaa ataaaatcac agttagagaa    3180
ccaaaaagct aaatgggaac aagagctctg cagtgtgaga ttgcctttaa atcaagaaga    3240
agagaagaga agaaatgtcg atatattaaa agaaaaaatt agacccgaag agcaacttag    3300 gaaaagtta gaagtgaaac accaacttga acagactctc agaatacaag atatagaatt    3360
gaaaagtgta acaagtaatt tgaatcaggt ttctcacact catgaaagtg aaaatgatct    3420
ctttcatgaa aattgcatgt tgaaaaagga aattgccatg ctaaaactgg aagtagccac    3480
actgaaacat caacaccagg tgaaggaaaa taaatacttt gaggacatta agattttaca    3540 agaaagaat gctgaacttc aaatgaccct aaaactgaaa cagaaaacag taacaaaaag    3600
ggcatctcag tatagagagc agcttaaagt tctgacggca gagaacacga tgctgacttc    3660
taaattgaag gaa                                                      3673
```

```
<210> SEQ ID NO 27
<211> LENGTH: 1011
<212> TYPE: PRT
<213> ORGANISM: Homo sapiens

<400> SEQUENCE: 27
```

```
Met Val Ala Thr Leu Leu Ser Tyr Gly Ala Val Ile Glu Val Gln Asn
1               5                   10                  15

Lys Ala Ser Leu Thr Pro Leu Leu Ala Ile Gln Lys Arg Ser Lys
            20                  25                  30

Gln Thr Val Glu Phe Leu Leu Thr Lys Asn Ala Asn Ala Asn Ala Phe
        35                  40                  45

Asn Glu Ser Lys Cys Thr Ala Leu Met Leu Ala Ile Cys Glu Gly Ser
    50                  55                  60

Ser Glu Ile Val Gly Met Leu Leu Gln Gln Asn Val Asp Val Phe Ala
65                  70                  75                  80

Glu Asp Ile His Gly Ile Thr Ala Glu Arg Tyr Ala Ala Ala Arg Gly
                85                  90                  95

Val Asn Tyr Ile His Gln Gln Leu Leu Glu His Ile Arg Lys Leu Pro
            100                 105                 110

Lys Asn Pro Gln Asn Thr Asn Pro Glu Gly Thr Ser Thr Gly Thr Pro
        115                 120                 125

Asp Glu Ala Ala Pro Leu Ala Glu Arg Thr Pro Asp Thr Ala Glu Ser
    130                 135                 140

Leu Leu Glu Lys Thr Pro Asp Glu Ala Ala Arg Leu Val Glu Gly Thr
145                 150                 155                 160

Ser Ala Lys Ile Gln Cys Leu Gly Lys Ala Thr Ser Gly Lys Phe Glu
                165                 170                 175
```

```
Gln Ser Thr Glu Glu Thr Pro Arg Lys Ile Leu Arg Pro Thr Lys Glu
            180                 185                 190

Thr Ser Glu Lys Phe Ser Trp Pro Ala Lys Glu Arg Ser Arg Lys Ile
            195                 200                 205

Thr Trp Glu Glu Lys Glu Thr Ser Val Lys Thr Glu Cys Val Ala Gly
            210                 215                 220

Val Thr Pro Asn Lys Thr Glu Val Leu Glu Lys Gly Thr Ser Asn Met
225                 230                 235                 240

Ile Ala Cys Pro Thr Lys Glu Thr Ser Thr Lys Ala Ser Thr Asn Val
                245                 250                 255

Asp Val Ser Ser Val Glu Pro Ile Phe Ser Leu Phe Gly Thr Arg Thr
            260                 265                 270

Ile Glu Asn Ser Gln Cys Thr Lys Val Glu Glu Asp Phe Asn Leu Ala
            275                 280                 285

Thr Lys Ile Ile Ser Lys Ser Ala Ala Gln Asn Tyr Thr Cys Leu Pro
            290                 295                 300

Asp Ala Thr Tyr Gln Lys Asp Ile Lys Thr Ile Asn His Lys Ile Glu
305                 310                 315                 320

Asp Gln Met Phe Pro Ser Glu Ser Lys Arg Glu Glu Asp Glu Glu Tyr
                325                 330                 335

Ser Trp Asp Ser Gly Ser Leu Phe Glu Ser Ser Ala Lys Thr Gln Val
            340                 345                 350

Cys Ile Pro Glu Ser Met Tyr Gln Lys Val Met Glu Ile Asn Arg Glu
            355                 360                 365

Val Glu Glu Leu Pro Glu Lys Pro Ser Ala Phe Lys Pro Ala Val Glu
            370                 375                 380

Met Gln Lys Thr Val Pro Asn Lys Ala Phe Glu Leu Lys Asn Glu Gln
385                 390                 395                 400

Thr Leu Arg Ala Ala Gln Met Phe Pro Ser Glu Ser Lys Gln Lys Asp
                405                 410                 415

Asp Glu Glu Asn Ser Trp Asp Ser Glu Ser Pro Cys Glu Thr Val Ser
            420                 425                 430

Gln Lys Asp Val Tyr Leu Pro Lys Ala Thr His Gln Lys Glu Phe Asp
            435                 440                 445

Thr Leu Ser Gly Lys Leu Glu Glu Ser Pro Val Lys Asp Gly Leu Leu
            450                 455                 460

Lys Pro Thr Cys Gly Arg Lys Val Ser Leu Pro Asn Lys Ala Leu Glu
465                 470                 475                 480

Leu Lys Asp Arg Glu Thr Phe Lys Ala Glu Ser Pro Asp Lys Asp Gly
                485                 490                 495

Leu Leu Lys Pro Thr Cys Gly Arg Lys Val Ser Leu Pro Asn Lys Ala
            500                 505                 510

Leu Glu Leu Lys Asp Arg Glu Thr Leu Lys Ala Glu Ser Pro Asp Asn
            515                 520                 525

Asp Gly Leu Leu Lys Pro Thr Cys Gly Arg Lys Val Ser Leu Pro Asn
530                 535                 540

Lys Ala Leu Glu Leu Lys Asp Arg Glu Thr Phe Lys Ala Ala Gln Met
545                 550                 555                 560

Phe Pro Ser Glu Ser Lys Gln Lys Asp Asp Glu Glu Asn Ser Trp Asp
                565                 570                 575

Phe Glu Ser Phe Leu Glu Thr Leu Leu Gln Asn Asp Val Cys Leu Pro
            580                 585                 590
```

-continued

```
Lys Ala Thr His Gln Lys Glu Phe Asp Thr Leu Ser Gly Lys Leu Glu
            595                 600                 605

Glu Ser Pro Asp Lys Asp Gly Leu Leu Lys Pro Thr Cys Gly Met Lys
        610                 615                 620

Ile Ser Leu Pro Asn Lys Ala Leu Glu Leu Lys Asp Arg Glu Thr Phe
625                 630                 635                 640

Lys Ala Glu Asp Val Ser Ser Val Glu Ser Thr Phe Ser Leu Phe Gly
                645                 650                 655

Lys Pro Thr Thr Glu Asn Ser Gln Ser Thr Lys Val Glu Glu Asp Phe
            660                 665                 670

Asn Leu Thr Thr Lys Glu Gly Ala Thr Lys Thr Val Thr Gly Gln Gln
        675                 680                 685

Glu Arg Asp Ile Gly Ile Ile Glu Arg Ala Pro Gln Asp Gln Thr Asn
690                 695                 700

Lys Met Pro Thr Ser Glu Leu Gly Arg Lys Glu Asp Thr Lys Ser Thr
705                 710                 715                 720

Ser Asp Ser Glu Ile Ile Ser Val Ser Asp Thr Gln Asn Tyr Glu Cys
                725                 730                 735

Leu Pro Glu Ala Thr Tyr Gln Lys Glu Ile Lys Thr Thr Asn Gly Lys
            740                 745                 750

Ile Glu Glu Ser Pro Glu Lys Pro Ser His Phe Glu Pro Ala Thr Glu
        755                 760                 765

Met Gln Asn Ser Val Pro Asn Lys Gly Leu Glu Trp Lys Asn Lys Gln
        770                 775                 780

Thr Leu Arg Ala Asp Ser Thr Thr Leu Ser Lys Ile Leu Asp Ala Leu
785                 790                 795                 800

Pro Ser Cys Glu Arg Gly Arg Glu Leu Lys Lys Asp Asn Cys Glu Gln
                805                 810                 815

Ile Thr Ala Lys Met Glu Gln Met Lys Asn Lys Phe Cys Val Leu Gln
            820                 825                 830

Lys Glu Leu Ser Glu Ala Lys Glu Ile Lys Ser Gln Leu Glu Asn Gln
            835                 840                 845

Lys Ala Lys Trp Glu Gln Glu Leu Cys Ser Val Arg Leu Pro Leu Asn
        850                 855                 860

Gln Glu Glu Glu Lys Arg Arg Asn Val Asp Ile Leu Lys Glu Lys Ile
865                 870                 875                 880

Arg Pro Glu Glu Gln Leu Arg Lys Leu Glu Val Lys His Gln Leu
                885                 890                 895

Glu Gln Thr Leu Arg Ile Gln Asp Ile Glu Leu Lys Ser Val Thr Ser
            900                 905                 910

Asn Leu Asn Gln Val Ser His Thr His Glu Ser Glu Asn Asp Leu Phe
        915                 920                 925

His Glu Asn Cys Met Leu Lys Lys Glu Ile Ala Met Leu Lys Leu Glu
930                 935                 940

Val Ala Thr Leu Lys His Gln His Gln Val Lys Glu Asn Lys Tyr Phe
945                 950                 955                 960

Glu Asp Ile Lys Ile Leu Gln Glu Lys Asn Ala Glu Leu Gln Met Thr
            965                 970                 975

Leu Lys Leu Lys Gln Lys Thr Val Thr Lys Arg Ala Ser Gln Tyr Arg
        980                 985                 990

Glu Gln Leu Lys Val Leu Thr Ala Glu Asn Thr Met Leu Thr Ser Lys
        995                 1000                1005

Leu Lys Glu
```

```
<210> SEQ ID NO 28
<211> LENGTH: 23
<212> TYPE: DNA
<213> ORGANISM: Homo sapiens

<400> SEQUENCE: 28
tctcatagat gctggtgctg atc                                              23

<210> SEQ ID NO 29
<211> LENGTH: 24
<212> TYPE: DNA
<213> ORGANISM: Homo sapiens

<400> SEQUENCE: 29
cccagacatt gaattttggc agac                                             24

<210> SEQ ID NO 30
<211> LENGTH: 56
<212> TYPE: PRT
<213> ORGANISM: Homo sapiens

<400> SEQUENCE: 30

Met Glu Glu Ile Ser Ala Ala Ala Val Lys Val Val Pro Gly Pro Glu
1               5                   10                  15

Arg Pro Ser Pro Phe Ser Gln Leu Val Tyr Thr Ser Asn Asp Ser Tyr
            20                  25                  30

Ile Val His Ser Gly Asp Leu Arg Lys Ile His Lys Ala Ala Ser Arg
        35                  40                  45

Gly Gln Val Arg Lys Leu Glu Lys
    50                  55
```